(12) United States Patent
Gordin et al.

(10) Patent No.: US 8,397,335 B2
(45) Date of Patent: Mar. 19, 2013

(54) DEVICE AND METHOD FOR LENS CLEANING FOR SURGICAL PROCEDURES

(75) Inventors: Udi Gordin, Tardion (IL); Gilad Heftman, Kibutz Ein-Gev (IL); Moran Sobol, Kibutz Gasher (IL); Amir Schvartzer, Hod Hasharon (IL); Amir Szold, Tel-Aviv (IL)

(73) Assignee: Virtual Ports Ltd., Misgav (IL)

( * ) Notice: Subject to any disclaimer, the term of this patent is extended or adjusted under 35 U.S.C. 154(b) by 825 days.

(21) Appl. No.: 12/418,030

(22) Filed: Apr. 3, 2009

(65) Prior Publication Data

US 2009/0250081 A1 Oct. 8, 2009

Related U.S. Application Data

(63) Continuation-in-part of application No. PCT/IL2007/001184, filed on Sep. 25, 2007.

(60) Provisional application No. 60/848,636, filed on Oct. 3, 2006.

(51) Int. Cl.
*A61B 1/00* (2006.01)
*B08B 9/00* (2006.01)

(52) U.S. Cl. ................. 15/104.05; 15/104.16
(58) Field of Classification Search .............. 15/104.05, 15/104.16
See application file for complete search history.

(56) References Cited

U.S. PATENT DOCUMENTS

| | | | |
|---|---|---|---|
| 3,182,373 A | 5/1965 | Strand | |
| 3,326,217 A | 6/1967 | Kerr | |
| 3,417,752 A | 12/1968 | Butler | |
| 4,106,508 A | 8/1978 | Berlin | |
| 4,112,951 A | 9/1978 | Hulka et al. | |
| 4,281,646 A | 8/1981 | Kinoshita | |
| 4,449,532 A | 5/1984 | Storz | |
| 5,312,426 A | 5/1994 | Segawa et al. | |
| 5,313,934 A | 5/1994 | Wiita et al. | |
| 5,351,675 A | 10/1994 | Brodsky | |
| 5,392,766 A * | 2/1995 | Masterson et al. | 600/157 |
| 5,400,767 A | 3/1995 | Murdoch | |
| 5,407,423 A * | 4/1995 | Yoon | 604/1 |

(Continued)

FOREIGN PATENT DOCUMENTS

EP 1648288 7/2004
WO 2003/013366 A2 2/2003

(Continued)

OTHER PUBLICATIONS

International Search Report published Dec. 10, 2009 for PCT/IL2009/00550 filed Jun. 2, 2009.

(Continued)

*Primary Examiner* — Randall Chin
(74) *Attorney, Agent, or Firm* — Martin Fleit; Paul D. Bianco; Fleit Gibbons Gutman Bongini Bianco PL

(57) ABSTRACT

The present invention provides a standalone cleaning device for cleaning at least a portion of a surgical instrument, especially the scope, within a body cavity during minimal invasive surgical procedure comprising, at least one cleansing mechanism characterized by an un-deployed configuration in which the device is inserted into the body cavity; and, a deployed configuration in which the portion of the surgical instrument is cleaned; the cleaning mechanism are adapted to be reversibly transformed from the deployed configuration to the un-deployed configuration and from the un-deployed configuration to the deployed configuration; wherein the cleaning of the surgical instrument is obtained by wiping motions of the portion of the surgical instrument over the cleansing material within the body cavity, such that the removal of the surgical instrument during the surgical procedure for cleaning necessity is avoided.

9 Claims, 23 Drawing Sheets

U.S. PATENT DOCUMENTS

| | | | |
|---|---|---|---|
| 5,549,543 A | 8/1996 | Kim | |
| 5,569,274 A | 10/1996 | Rapacki et al. | |
| 5,910,106 A | 6/1999 | Morgan et al. | |
| 6,206,827 B1 | 3/2001 | Chin et al. | |
| 6,354,992 B1 | 3/2002 | Kato | |
| 6,358,196 B1 | 3/2002 | Rayman | |
| 6,494,211 B1 | 12/2002 | Boyd et al. | |
| 6,607,475 B2 | 8/2003 | Doyle et al. | |
| 6,814,742 B2 | 11/2004 | Kimura et al. | |
| 7,311,660 B2 | 12/2007 | Gomez | |
| 7,854,728 B2 * | 12/2010 | Boyle, Jr. ................. | 604/267 |
| 2002/0022762 A1 | 2/2002 | Beane et al. | |
| 2003/0009080 A1 | 1/2003 | Peng et al. | |
| 2005/0171493 A1 * | 8/2005 | Nicholls ................. | 604/267 |
| 2005/0251183 A1 | 11/2005 | Buckman et al. | |
| 2005/0283137 A1 | 12/2005 | Doyle et al. | |
| 2006/0149135 A1 | 7/2006 | Paz | |
| 2008/0064927 A1 | 3/2008 | Larkin et al. | |
| 2009/0209947 A1 | 8/2009 | Gordin et al. | |
| 2009/0222029 A1 | 9/2009 | Gordin et al. | |
| 2011/0124962 A1 | 5/2011 | Gordin | |

FOREIGN PATENT DOCUMENTS

| | | |
|---|---|---|
| WO | 2005/002415 A2 | 1/2005 |
| WO | 2008/041225 A2 | 4/2008 |
| WO | 2008/041226 A2 | 4/2008 |
| WO | 2008/041227 A2 | 4/2008 |

OTHER PUBLICATIONS

Written Opinion of the International Searching Authority mailed Sep. 29, 2009 for PCT/IL2009/00550 filed Jun. 2, 2009.
International Preliminary Report on Patentability published Dec. 6, 2010 for PCT/IL2009/00550 filed Jun. 2, 2009.
U.S. Appl. No. 60/848,636, filed Oct. 3, 2006.
International Preliminary Report on Patentability issued Aug. 4, 2009 for PCT/IL2007/001186 filed Sep. 25, 2007.
International Preliminary Report on Patentability issued Apr. 7, 2009 for PCT/IL2007/001185 filed Sep. 25, 2007.
International Preliminary Report on Patentability issued Apr. 7, 2009 for PCT/IL2007/001184 filed Sep. 25, 2007.
International Search Report mailed Jun. 18, 2008 for PCT/IL2007/001184 filed Sep. 25, 2007.
Written Opinion mailed Jun. 18, 2008 for PCT/IL2007/001184 filed Sep. 25, 2007.
International Search Report mailed Sep. 9, 2008 for PCT/IL2007/001185 filed Sep. 25, 2007.
Written Opinion mailed Sep. 9, 2008 for PCT/IL2007/001185 filed Sep. 25, 2007.
International Search Report mailed Mar. 10, 2009 for PCT/IL2007/001186 filed Sep. 25, 2007.
Written Opinion mailed Mar. 10, 2009 for PCT/IL2007/001186 filed Sep. 25, 2007.
Office Action mailed Nov. 1, 2011 for U.S. Appl. No. 12/418,094, filed Apr. 3, 2009.
Restriction Requirement mailed on Jul. 27, 2011 for U.S. Appl. No. 12/418,094, filed Apr. 3, 2009.
Response to Restriction Requirement filed Aug. 23, 2011 for Restriction Requirement mailed on Jul. 27, 2011 for U.S. Appl. No. 12/418,094, filed Apr. 3, 2009.
Response to Office Action for U.S. Appl. No. 12/418,094 submitted Mar. 25, 2012.

* cited by examiner

DEVICE AND METHOD FOR LENS CLEANING FOR SURGICAL PROCEDURES

CROSS REFERENCE TO RELATED APPLICATIONS

This application is a continuation-in-part application of International Application No. PCT/IL2007/001184, filed 25 Sep. 2007, which claims priority to U.S. Provisional Application No. 60/848,636, filed Oct. 3, 2006. The entire contents of each of these applications are incorporated herein by reference.

FIELD OF THE INVENTION

The present invention generally relates to cleaning scope lens during minimally invasive surgery.

BACKGROUND OF THE INVENTION

Endoscopic interventions represent a significant advance in various fields of surgery permitting the performance of the majority of interventions through a number of small incisions reducing postoperative pain and enhancing the postoperative recovery.

In endoscopic surgery, the surgeon performs the operation through small holes using long instruments and observing the internal anatomy with an endoscope camera.

Endoscopy is a minimally invasive medical procedure, used to evaluate the interior cavities of the body by inserting a small scope in the body. The endoscope usually comprises a light source to illuminate the organ under inspection, and a viewing means which transmits images from inside the body to a receiver and a recorder for capture of the video images. The interior surfaces are viewed through the eyepiece of the scope. The objective lens of the scope is frequently soiled or obscured during operative procedures by fog, blood, other body fluids or tissue particles. When this occurs, the surgeon has to remove the scope from the body cavity and clean the objective lens with a wipe. During some operative procedures, the surgeon is frequently disturbed by removing the scope.

U.S. Pat. No. 4,281,646 to Kinoshita discloses a cleaning device comprises a fluid passage extending through the sheath of a forward view type endoscope and having one end located in the operation section of the endoscope and the other end located in the distal end section of the endoscope; a pump for supplying a fluid through the fluid passage from the operation section; a nozzle disposed in the distal end portion and communicating at its proximal end with said other end of the fluid passage; a reciprocating device for projecting the distal end portion of the nozzle from the distal end of the distal end section and retracting the nozzle into the distal end section; and a nozzle opening which is directed to an observation window provided on the distal end when the nozzle is projected from the distal end and which is closed by the distal end section.

U.S. Pat. No. 5,313,934 to Wiita et. al. discloses a hollow tubular elongated member is concentrically mounted to a borescope or surgical viewing instrument defining a spaced passage for flowing fluid to a cuff which is discretely located below the distal end of the lens of the borescope and which defines a discretely configured discharge port for flowing fluid over the lens surface for cleansing and defogging purposes. A two-piece locking handle may be used to lock the lens cleaning apparatus to the borescope. Another embodiment includes a flexible tube utilized with the cuff; a defined space within a sheath for passage of cleansing fluid. The cleansing fluid is directed by a discharge port onto the lens for cleansing and defogging.

U.S. Pat. No. 5,400,767 to Murdoch discloses a device for cleaning the objective lens of a laparoscope, endoscope, coeloscope or similar telescope, without the removal of said telescope from the body cavity. In one embodiment, the device consists of a tube, the inner diameter of which is such that it accepts the shaft of such telescope. On the inner circumference, near to or at one end of the tube, is a ridge that can direct a flow of fluid within the tube onto the objective lens at the end of a telescope shaft inserted within the tube. At the other end of the tube there is a means of making a seal, such as a flexible O-ring, that prevents or reduces the leakage of air and/or fluid between the tube and the inserted shaft of the telescope. There is an aperture in the tube which gives access to the inside of the tube. Prior to use, the shaft of the telescope is inserted into the invention so that the end of the telescope, containing the objective lens, touches or almost touches the ridge. During operation, whenever the objective lens at the end of the telescope shaft becomes soiled or obscured, fluid is injected through the aperture via a fixture. The fluid flows between the telescope shaft and the inner wall of the tube until it reaches the ridge which directs the fluid over the objective lens, washing the lens and improving or restoring visibility.

U.S. Pat. No. 6,354,992 to Kato discloses an apparatus and method for cleaning the objective lens of a laparoscope, endoscope, or coeloscope during surgery and also removing the solution and debris during and after the cleaning. The result is obtained by using a rigid hollow split sheath for the scope. The split sheath has two separate channels. One channel is for irrigation and the cleaning fluid flows through this channel to be directed onto the lens. The other channel is for suction to remove the solution and debris during and after the cleaning. Control buttons located at the operator's end activate the irrigation and suction functions. The control buttons for irrigation and suction are fabricated into an existing valve type device which can regulate either of these functions. In addition, two ports, one for irrigation and one for suction emerge from the operator's end to connect to the appropriate tubing for irrigation and suction. A rubber ring device screws down at the operator's end allowing the surgeon to secure the sheath to the scope and prevent any leakage of the standard carbon dioxide gas used to distend the abdomen for operative laparoscopy in the patient. However, the above mentioned devices should be incorporated with an endoscope or be attached to the endoscope. Therefore, all the solutions proposed above are not standalone solutions.

Thus, there is a need for a standalone solution for cleaning endoscope lens which will be independent of the endoscope and will not require additional incisions. Moreover, these prior art solutions introduce fluid and/or gas pressure onto the lens and into the body cavity. This method is not optimized for cleaning fat-based soiling from the lens. An efficient method to clean the scope is by using a fabric or an absorbing means. Therefore, there is a need for providing a device, system and method for cleaning the scope inside the cavity by wiping the lens on an absorbing means without the need to remove the scope from the cavity during a surgical procedure.

SUMMARY OF THE INVENTION

It is one object of the invention to disclose a cleaning device for cleaning surgical instruments, especially the scope lens and/or the tip of the scope and/or the cover of the scope; wherein said cleaning device is adapted to clean said surgical instruments, especially said scope lens and/or said tip of said scope and/or said cover of said scope by wiping said surgical instrument over said cleaning device during a surgical procedure within the abdominal cavity and/or within a hollow body organs and/or natural/artificial orifices and/or spaces and/or post operative spaces; Further wherein said cleaning device is a standalone cleaning device.

It is also an object of the invention to disclose the cleaning device as defined above, wherein the removal of said surgical instrument during said surgical procedure for cleaning necessity is avoided.

It is also an object of the invention to disclose the cleaning device as defined above, additionally comprising anchoring means; said anchoring means anchors said cleaning device to internal walls within the abdominal cavity and/or within a hollow body organs and/or natural/artificial orifices and/or spaces and/or post operative spaces, prior to and/or during surgical procedure.

It is also an object of the invention to disclose the cleaning device as defined above, wherein said anchoring means are releasable means.

It is also an object of the invention to disclose the cleaning device as defined above, wherein said anchoring means are selected from a group comprising mechanical anchoring means, especially grabber of two jaws means, piercing with arrow shaped tack means, magnetic anchoring means, suction anchoring means, adhesive anchoring means, or any combination of these means.

It is also an object of the invention to disclose the cleaning device as defined above, wherein said cleaning device assumes its closed configuration prior to inserting said cleaning device within said abdominal cavity and/or within said hollow body organs and/or said natural/artificial orifices and/or said spaces and/or said post operative spaces.

It is also an object of the invention to disclose the cleaning device as defined above, wherein said cleaning device assumes its open configuration within said abdominal cavity and/or within said hollow body organs and/or said natural/artificial orifices and/or said spaces and/or said post operative spaces.

It is also an object of the invention to disclose the cleaning device as defined above, wherein said cleaning device assumes its open configuration within said abdominal cavity and/or within said hollow body organs and/or said natural/artificial orifices and/or said spaces and/or said post operative spaces prior to and/or during said surgical procedure; further wherein said cleaning device assumes its closed configuration prior to and/or during the extraction of said cleaning device from said abdominal cavity and/or within said hollow body organs and/or said natural/artificial orifices and/or said spaces and/or said post operative spaces through an incision and/or a trocar and/or a natural orifice.

It is also an object of the invention to disclose the cleaning device as defined above, additionally comprising: (a) a trocar; and (b) at least one cleansing material; said cleaning material surrounds said trocar; said trocar is simultaneously used for introducing other surgical instrument to said body cavity and/or said abdominal cavity and/or said hollow body organs and/or said natural/artificial orifices and/or said spaces and/or said post operative spaces.

It is also an object of the invention to disclose the cleaning device as defined above, wherein the cleaning of said surgical instrument and/or said scope lens and/or said tip of the scope and/or said cover of the scope is obtained by wiping motions of said surgical instrument and/or said scope lens and/or said tip of the scope and/or said cover of the scope over said cleansing material.

It is also an object of the invention to disclose the cleaning device as defined above, wherein said cleaning device is made of a group comprising of biodegradable materials and/or shape memory materials.

It is also an object of the invention to disclose the cleaning device as defined above, wherein said cleaning device is provided with a hook or loop engagement means for engagement with said introducer.

It is also an object of the invention to disclose the cleaning device as defined above, additionally comprising means to allow said cleaning device to move from one position to another.

It is also an object of the invention to disclose a system for use during a surgical procedure. The system comprising: (a) at least one cleaning device as defined above; and (b) at least one introducer; wherein said cleaning device introduced via said introducer into an abdominal cavity and/or to a body cavity and/or to an organ and/or to a hollow body organ and/or natural/artificial orifice and/or spaces and/or post operative spaces, prior to and/or during any surgical procedure; further wherein said cleaning device is adapted to clean said surgical instruments, especially said scope lens and/or said tip of said scope and/or said cover of said scope by wiping said surgical instrument over said device during a surgical procedure within the body cavity and/or abdominal cavity and/or a hollow body organ and/or natural/artificial orifices and/or spaces and/or post operative spaces, during any surgical procedure; further wherein said cleaning device is a standalone device.

It is also an object of the invention to disclose the system as defined above, wherein said cleaning device is made of a group comprising of biodegradable materials and/or shape memory materials.

It is also an object of the invention to disclose the system as defined above, additionally comprising means to allow said cleaning device to move from one position to another.

It is also an object of the invention to disclose the system as defined above, wherein said cleaning device is provided with a hook or loop engagement means for engagement with said introducer.

It is also an object of the invention to disclose the system as defined above, wherein said introducer is adapted to introduce said device into said body cavity and/or said abdominal cavity and/or into said hollow body organs and/or into said natural/artificial orifices and/or into said spaces and/or into said post operative spaces, prior to and/or during a surgical procedure It is also an object of the invention to disclose the system as defined above, wherein said introducer is disconnect from said cleaning device within said body cavity and/or said abdominal cavity and/or said hollow body organs and/or said natural/artificial orifices and/or said spaces and/or said post operative spaces, prior to and/or during a surgical procedure.

It is also an object of the invention to disclose the system as defined above, wherein said introducer is adapted to reconnect to said cleaning device within said body cavity and/or abdominal cavity and/or said hollow body organs and/or said natural/artificial orifices and/or said spaces and/or said post operative spaces, prior to and/or during a surgical procedure.

It is also an object of the invention to disclose the system as defined above, wherein said introducer is adapted to transfer said cleaning device from its open configuration to its closed configuration.

It is also an object of the invention to disclose the system as defined above, wherein said introducer is adapted to extract said cleaning device from within said body cavity and/or said abdominal cavity and/or said hollow body organs and/or said natural/artificial orifices and/or said spaces and/or said post operative spaces.

It is also an object of the invention to disclose the system as defined above, wherein said introducer engages said cleaning device by a hook and loop engagement means.

It is also an object of the invention to disclose the system as defined above, additionally comprising anchoring means; said anchoring means anchors said cleaning device to said internal walls within the abdominal cavity and/or to said internal walls within the body cavity and/or to said organ and/or to said internal walls within hollow body organs and/or to said internal walls within natural/artificial orifices and/or to said internal walls within spaces and/or post operative spaces, prior to and/or during a surgical procedure.

It is also an object of the invention to disclose a method for cleaning and/or improving and/or restoring visibility of surgical instruments, especially the scope lens and/or the tip of the scope and/or the cover of the scope and/or camera lens, useful for surgical procedures. The method comprises steps selected inter alia from (a) obtaining a system as defined above; (b) inserting said cleaning device through an incision into to a body cavity and/or to an organ and/or to a hollow body organ and/or natural/artificial orifices and/or spaces and/or post operative spaces in its closed configuration using the introducer; (c) disconnecting said introducer from said cleaning device; and (d) cleaning said surgical instrument scope lens and/or the tip of the scope and/or the cover of the scope and/or camera lens by wiping said surgical instrument over said cleaning device; wherein an additional incision for passage or introduction of cleaning apparatus or implements is rendered unnecessary.

It is also an object of the invention to disclose the method as defined above, additionally comprising the step of anchoring said cleaning device via said introducer to said internal walls of said body cavity and/or to said organ and/or to said internal walls of hollow body organs and/or to said internal walls of natural/artificial orifices and/or to said internal walls of spaces and/or to said post operative spaces.

It is also an object of the invention to disclose the method as defined above, additionally comprising the step of re-cleaning said surgical instrument according to a predetermined medical need.

It is also an object of the invention to disclose the method as defined above, additionally comprising the step of releasing and reattaching said cleaning means to an undersurface of said body cavity and/or to said organ and/or to said hollow body organs and/or to said natural/artificial orifices and/or to said spaces and/or to said post operative spaces.

It is also an object of the invention to disclose the method as defined above, additionally comprising the step of reconnecting said cleaning device to said introducer.

It is still an object of the invention to disclose the method as defined above, additionally comprising the step of extracting said cleaning device means via said introducer.

It is lastly an object of the invention to disclose the method as defined above, additionally comprising the step of selecting said anchoring means from a group comprising magnetic anchoring means, suction anchoring, adhesive anchoring, mechanical anchoring, especially hook anchoring or other minimally invasive means, any combination of these means, or other non-invasive or minimally invasive anchoring means.

BRIEF DESCRIPTION OF THE FIGURES

In order to understand the invention and to see how it may be implemented in practice, and by way of non-limiting example only, with reference to the accompanying drawing, in which.

DETAILED DESCRIPTION OF PREFERRED EMBODIMENTS

Figure 1:
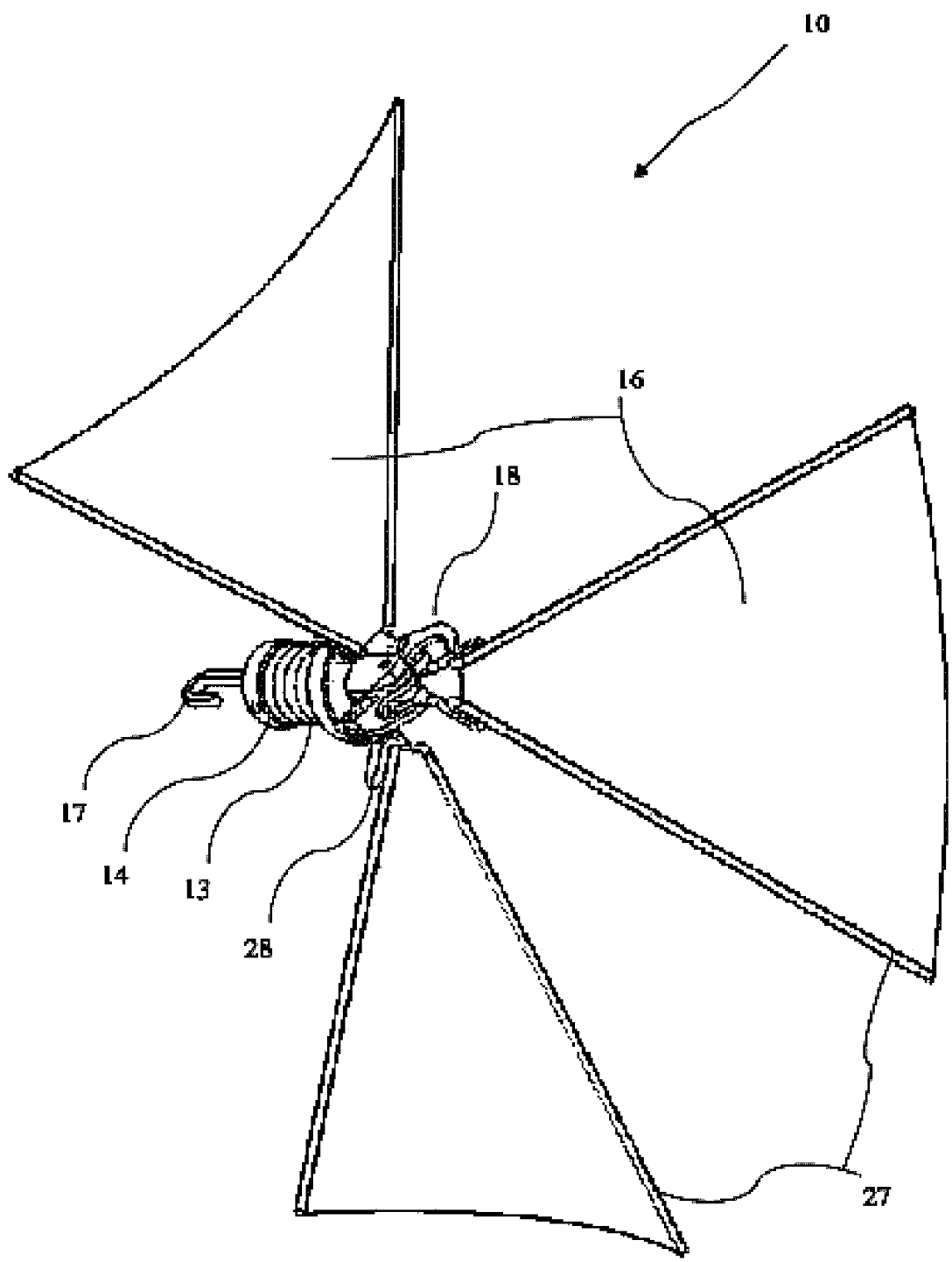
FIG. 1 is a perspective schematic view of an anchorable cleaning device, according to one embodiment of the present invention, in its open configuration.

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a lens cleaner device system and method to use during an endoscopic surgery.

U.S. application Ser. No. 10/563,229, now U.S. Pat. No. 8,038,612, PCT publication no. WO2005/002415, and EP Application No 04 744 933.5 are incorporated in all its parts as a reference to the current invention. Exemplary descriptions and embodiments of the anchoring of the cleaning device are found in U.S. application Ser. No. 10/563,229, now U.S. Pat. No. 8,038,612, PCT publication no. WO2005/002415, and EP Application No 04 744 933.5.

It is an object of the present invention to provide an efficient, disposable cleaning means such as fabric, sponge or any other absorbing material or material for rubbing used for cleaning the camera lens during an endoscopic surgical procedure. Such means would be used within the body cavity during the surgical procedure, avoiding the scope removal and without disturbing the surgeon.

The present invention also provides a cleaning device for cleaning surgical instruments, especially the scope lens and/or the tip of the scope and/or the cover of the scope. The cleaning device is adapted to clean the surgical instruments, especially the scope lens and/or the tip of said scope and/or the cover of the scope by wiping the surgical instrument over the cleaning device during a surgical procedure within the abdominal cavity and/or within a hollow body organs and/or natural/artificial orifices and/or spaces and/or post operative spaces. The cleaning device is a standalone cleaning device.

Another aspect of the present invention is a system including the cleaning device and an introducer which introduces the device into cavity, manipulates the device and disconnects from the device inside the cavity, so it can be applied without the need of additional significant incisions in the cavity or additional trocars.

The present invention also provides a system for use during a surgical procedure. The system comprising:

(a) at least one cleaning device; and, (b) at least one introducer.

The cleaning device introduced via said introducer into an abdominal cavity and/or to a body cavity and/or to an organ and/or to a hollow body organ and/or natural/artificial orifice and/or spaces and/or post operative spaces, prior to and/or during any surgical procedure. The cleaning device is adapted to clean said surgical instruments, especially said scope lens and/or the tip of the scope and/or the cover of the scope by wiping the surgical instrument over the device during a surgical procedure within the body cavity and/or abdominal cavity and/or a hollow body organ and/or natural/artificial orifices and/or spaces and/or post operative spaces, during any surgical procedure. The cleaning device is a standalone device.

Another aspect of the present invention is a method for cleaning surgical instruments by which a cleaning means is introduced in the body cavity in its closed configuration prior to the medical procedure, attached to the undersurface of the cavity or to an organ and deployed to its spread configuration to permit cleaning of the lens of the instrument, by pressing and rubbing the scope against this cleaning means in a wiping motion, intermittently and repeatedly during the procedure.

The present invention also provides a method for cleaning and/or improving and/or restoring visibility of surgical instruments, especially the scope lens and/or the tip of the scope and/or the cover of the scope and/or camera lens, useful for surgical procedures. The method comprises steps selected inter alia from:

(a) obtaining a system; (b) inserting said cleaning device through an incision into to a body cavity and/or to an organ and/or to a hollow body organ and/or natural/artificial orifices and/or spaces and/or post operative spaces in its closed configuration using the introducer; (c) disconnecting the introducer from the cleaning device; and, (d) cleaning said surgical instrument scope lens and/or the tip of the scope and/or the cover of the scope and/or camera lens by wiping said surgical instrument over the cleaning device. Any an additional incision for passage or introduction of cleaning apparatus or implements is rendered unnecessary.

The term "endoscopic surgery" refers hereinafter to procedures performed inside the body through small incisions or within the lumen of an organ with the aid of a special camera.

The term "endoscopic instruments" refers hereinafter to surgical instrument or devices used during endoscopic surgery.

The term "minimally invasive surgery" refers hereinafter to a procedure that is carried out by entering the body through the skin or through a body cavity or anatomical opening, but with the smallest damage possible.

The term "body cavity" refers hereinafter to any cavity within the body such as internal walls of the abdominal cavity and/or within hollow body organs and/or within the natural/artificial orifices and/or within the spaces and/or to the post operative spaces.

The term "trocar" refers hereinafter to a surgical instrument passed through the body, used to allow easy exchange of endoscopic instruments during endoscopic surgery.

The term 'scope' refers hereinafter to a laparoscope, endoscope, rigid endoscope, flex endoscope, ceroscopy or optical device used for observation within a body cavity and/or procedures being performed within a body cavity.

The term "introducer" refers hereinafter to any surgical instrument specially designed for providing access during a surgery or operation.

The term "standalone" refers hereinafter to any accessories independent of the scope type or manufacturer and that should not be engaged to the scope for the entire procedure.

Figure 21:
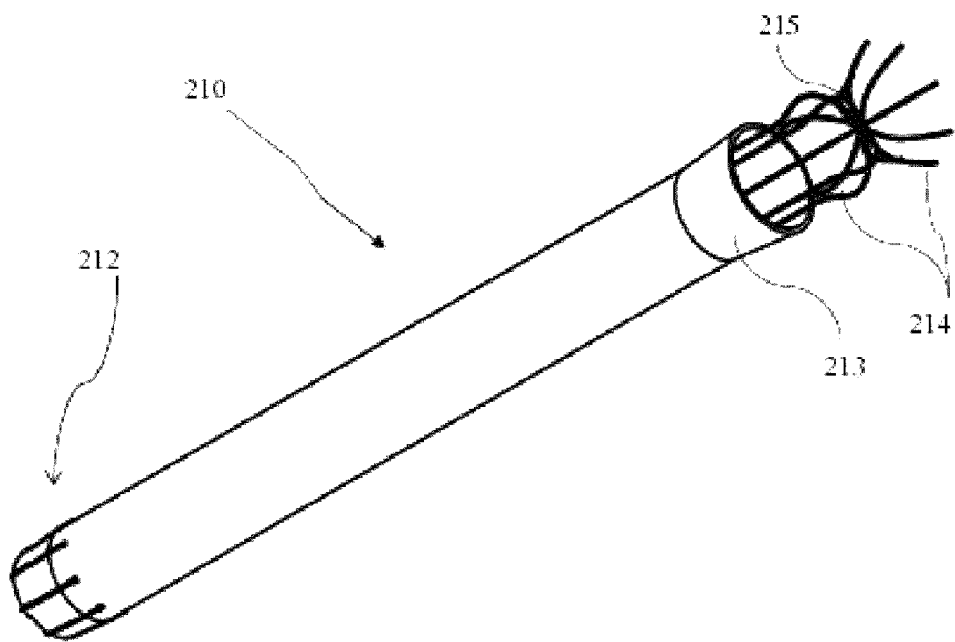
FIG. 21 is a perspective schematic view of a trocar tube with cleaning material at its distal end, in its undeployed configuration, according to one embodiment of the present invention.

The term "closed configuration" or "up-deployed configuration" refers hereinafter to the cleaning device's configuration which enables the cleaning device to be inserted to or extracted from the body cavity and/or the abdominal cavity and/or the hollow body organs and/or the natural/artificial orifices and/or the spaces and/or the post operative spaces through an incision and/or a trocar and/or a natural orifice (see for example FIGS. 2, 5 and 8 for the first embodiment, FIG. 14 for the second embodiment—tent like shape; and, FIG. 21 for the third embodiment—an integrated trocar with a cleaning device).

Figure 24:
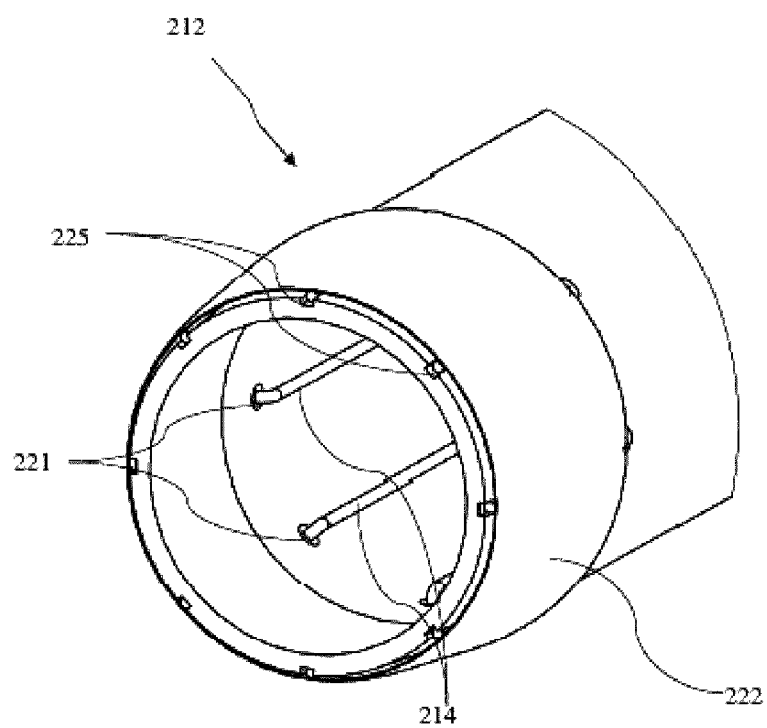
FIG. 24 is an enlarged view of FIG. 22 focused on the distal end of the trocar tube.

The term "open configuration" or "deployed configuration" refers hereinafter to the optimal working configuration of the cleaning device. I.e., in this configuration the surgical instrument can be cleaned (see for example FIGS. 1, 4, 7 and 10 for the first embodiment, FIG. 13 for the second embodiment—tent-like shape; and, FIG. 24 for the third embodiment—an integrated trocar with a cleaning device).

The term "biocompatible materials" refers hereinafter to materials that have the ability to perform with an appropriate host response in a specific application. Biocompatible materials have the quality of not having toxic or injurious effects on biological systems.

The term "shape memory materials" refers hereinafter to materials which can "remember" there original geometry. After a sample of shape memory materials has been deformed from its original geometry, it regains its original geometry by itself during heating (one-way effect) or, at higher ambient temperatures, simply during unloading (pseudo-elasticity or super-elasticity). The thermally induced shape-memory effect has been described for different material classes: polymers, such as polyurethanes, poly(styrene-block-butadiene), polydioxanone and polynorbornene, metallic alloys, such as copper-zinc-aluminum-nickel, copper-aluminum-nickel, and nickel-titanium (NiTi) alloys.

The term "biodegradable materials" refers hereinafter to materials that are degrade by the body's enzymatic pathways through a reaction against "foreign" material.

The term "surgical instruments" refers hereinafter to any surgical instrument used while performing a minimal invasive surgery, especially the scope lens and/or the tip of the scope and/or the cover of the scope.

The term "wiping" refers hereinafter to any rubbing in order to clean or remove any dirt or unwanted particles from the scope of the surgical instruments.

Figure 2:
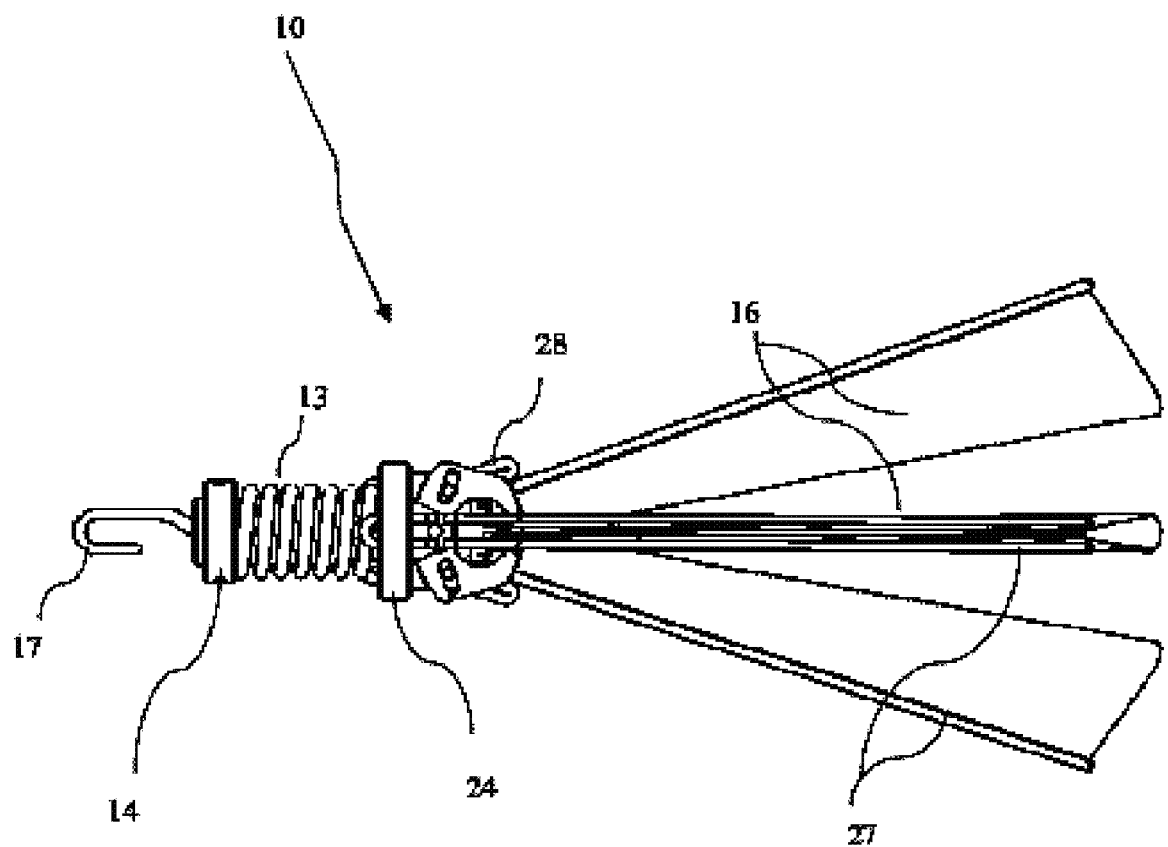
FIG. 2 is a side view of the same, in its closed configuration.
Figure 3:
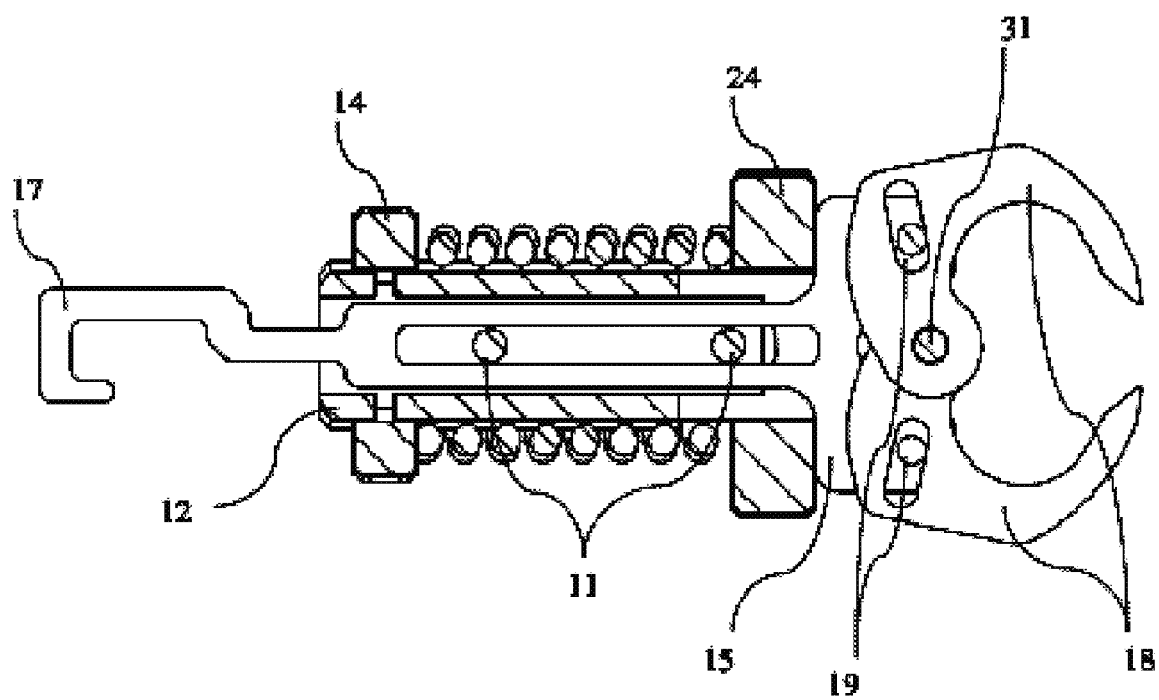
FIG. 3 is an enlarged sectional view of FIG. 2, focused on the mechanism.

Reference is now made to FIGS. 1-3 which schematically display the anchoring cleaning device (10). An anchorable assembly 10 comprises a tubular member 12 surrounded by a spring 13 set between two abutments rings 14 (proximal) and 24 (distal). A plurality of cleansing vanes 16 are attached to the distal ring 24 by means of supporting wires 27. The cleansing material of the vane 16 is attached to the wire 11 by means of a biocompatible adhesive. Between the distal ring 24 and the cleansing vane 16, the wires 27 are bent into a tight "S" shape 28 in order to improve the response to the stresses experienced during the anchoring of the device to the peritoneum of the abdominal internal wall and when the device is reinserted into the sleeve (see item 166 in FIGS. 19 and 20) of an introducer device 160 (in order to protect to the undeployed cleansing vanes 16 when the device is reinserted into the sleeve). A plate 15, with a hook at its proximal end 17 for engaging an introducer device 160, can slide axially within the body of the device and by the means of two pins 19 manipulates the two anchoring jaws 18. Pulling on the hook 17 the two pins 19 attached to the plate 15 cause the opening of the two anchoring jaws 18 about an axis pin 31 attached to the device body 12. The device 10 can then be anchored to the undersurface of the cavity wall by closing the anchoring jaws 18 in a pinching fashion on the wall. To achieve the pinching action, when the force ceases to be applied, the spring 13 pushes on the distal ring 24 which in turn pushes on the hook 17 and moves it distally, thus the pins 19 cause the closing of the anchoring jaws 18 about the axis pin 31.

Figure 4:
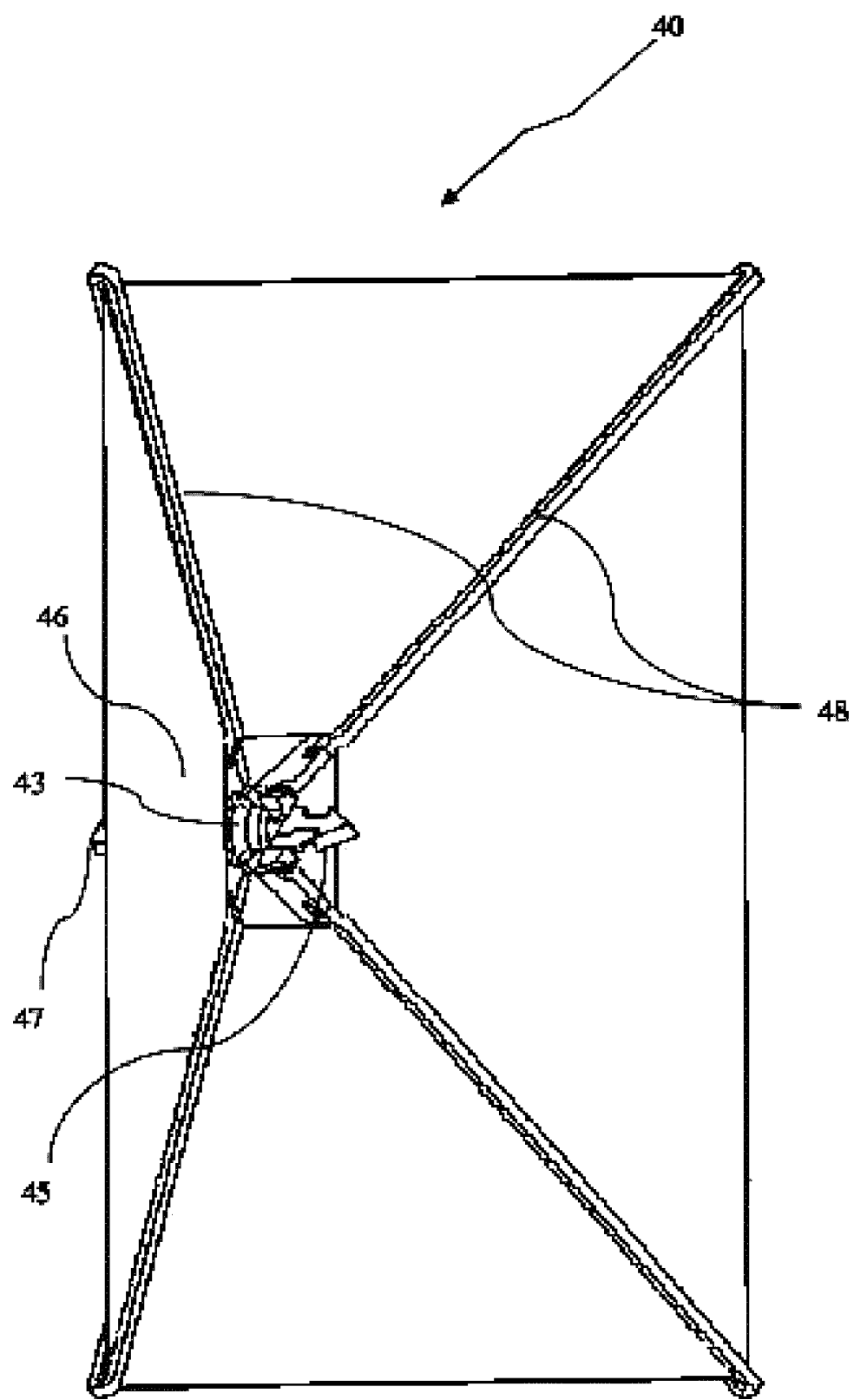
FIG. 4 is a perspective schematic view of an anchorable cleaning device, according to another embodiment of the present invention, in its open configuration.
Figure 5:
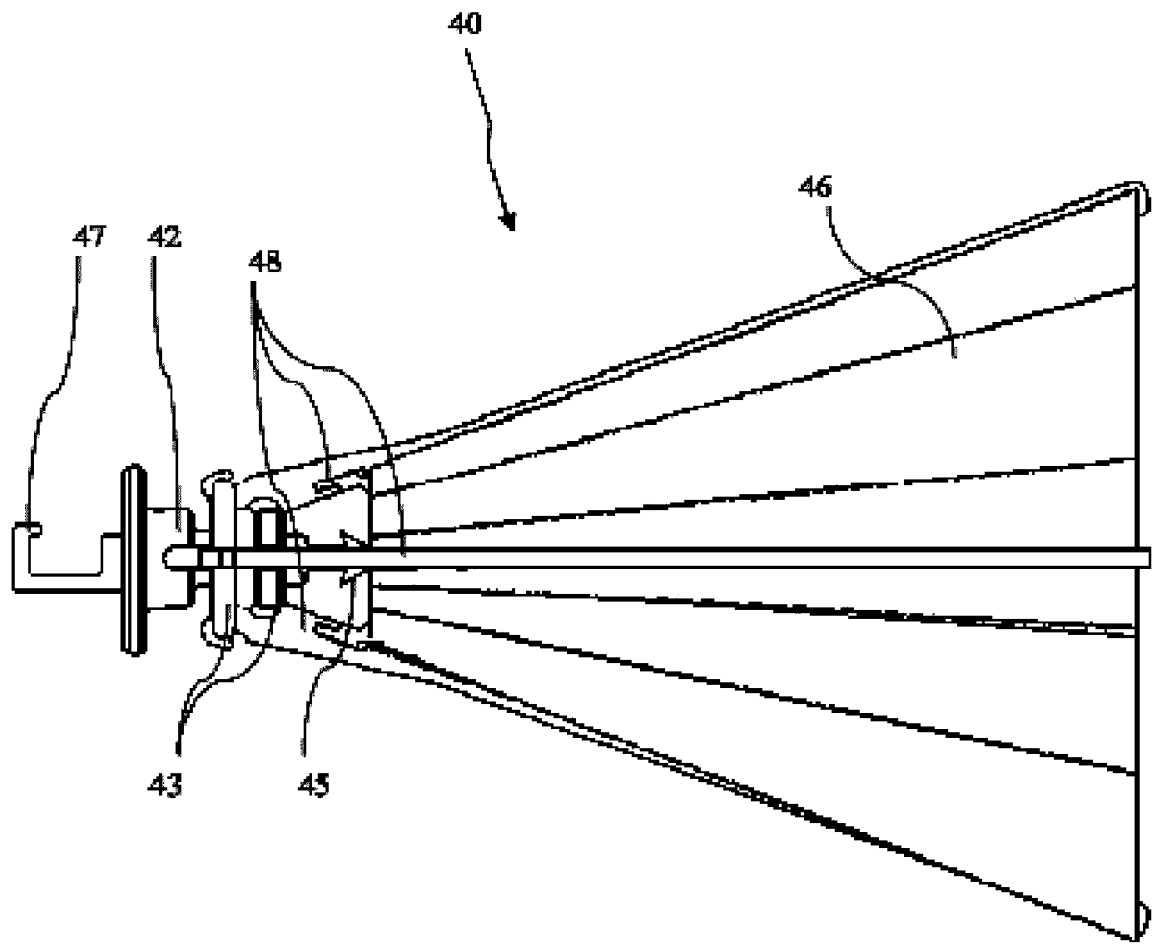
FIG. 5 is a side view of the same, in its closed configuration.
Figure 6:
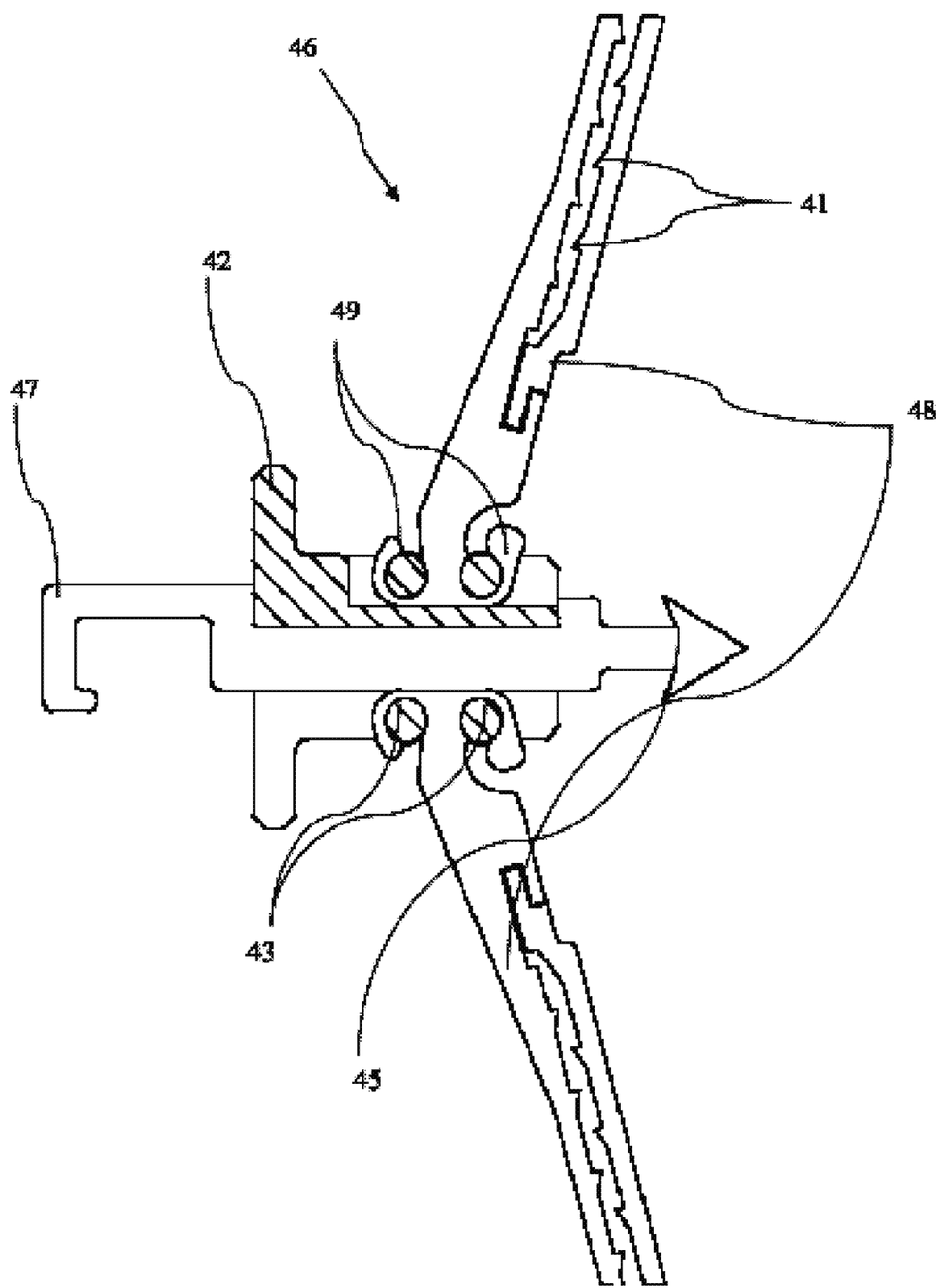
FIG. 6 is an enlarged sectional view of FIG. 5, focused on the mechanism.

Reference is now made to FIGS. 4-6 which schematically display another anchoring cleaning device. Anchorable assembly 40 comprises a tubular member 42 surrounded by two o-rigs 43. The o-rings 43 hold in place four clasping arms 48 at their hinging end 49. The clasping arms 48 hold in place a piece of cleansing material 46 by means of grasping teeth 41. The o-rings 43 allow the deployment and un-deployment of the device, such that the clasping arms 48 can be folded towards each other thus folding the cleansing material 46, so that the whole device can enter the sleeve (166) of an introducer device. Within the tubular member 42 resides an arrow shaped tack 45 with a hook at its proximal end 47 for engaging an introducer device 160 The device 40 can be anchored to the undersurface of the cavity wall by piercing it with the arrow shaped tack 45.

Figure 7:
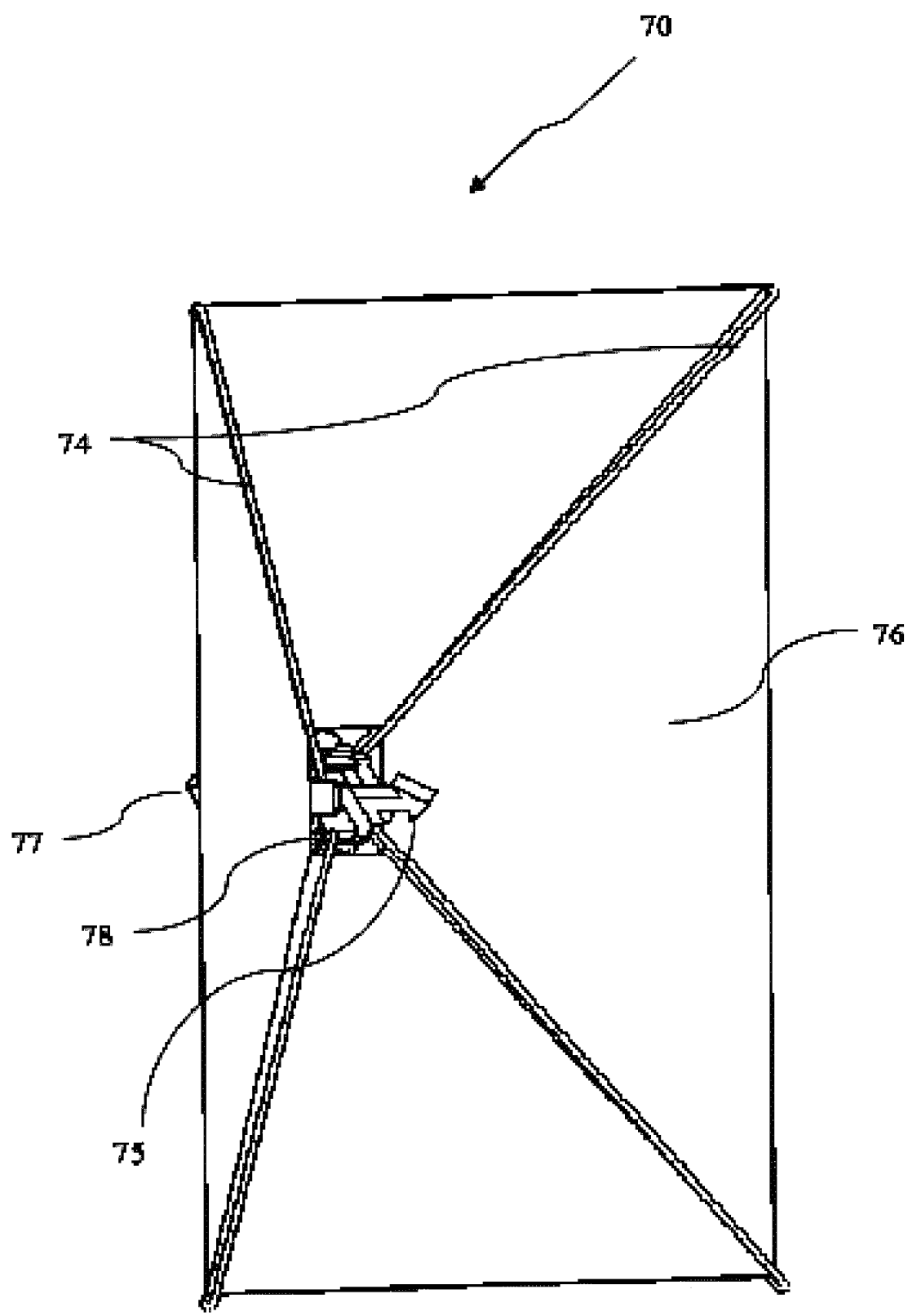
FIG. 7 is a perspective schematic view of an anchorable cleaning device, according to yet another embodiment of the present invention, in its open configuration.
Figure 8:
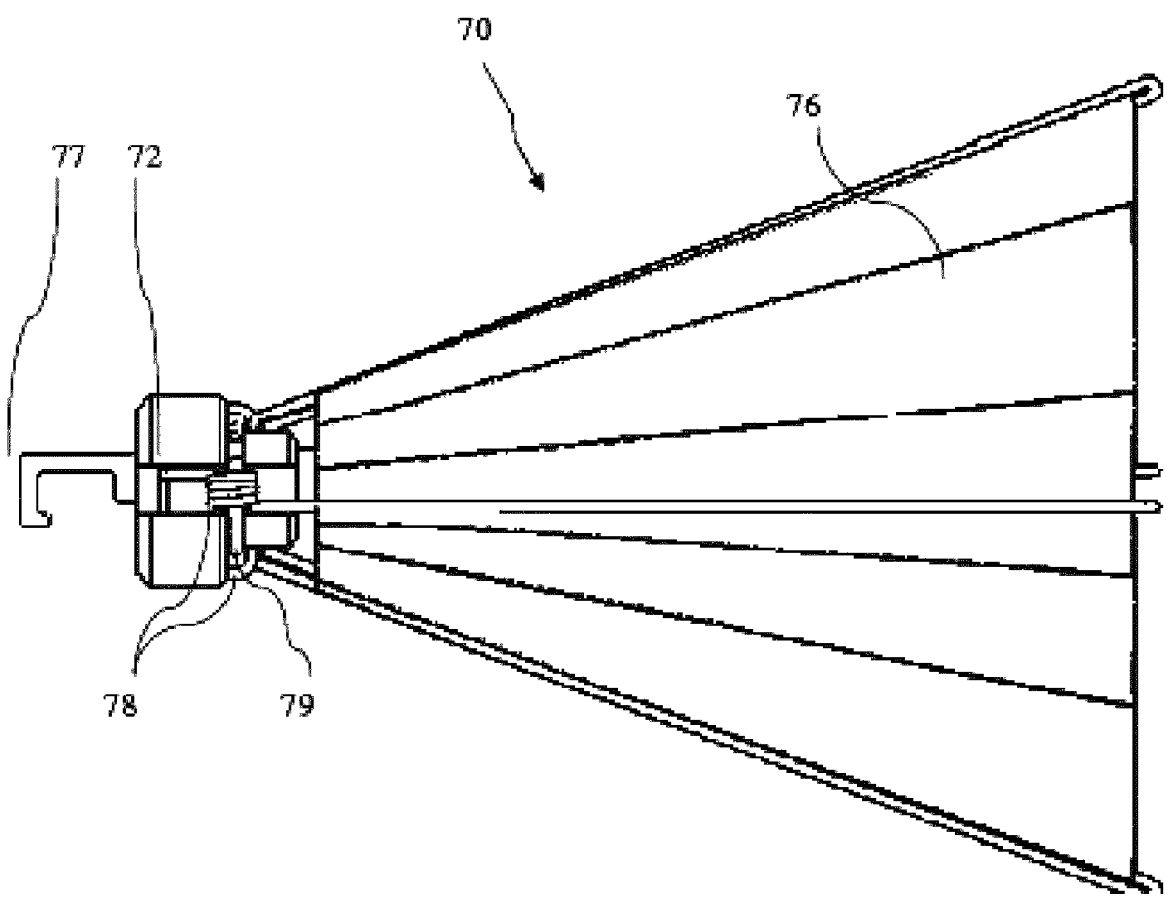
FIG. 8 is a side view of the same, in its closed configuration.
Figure 9:
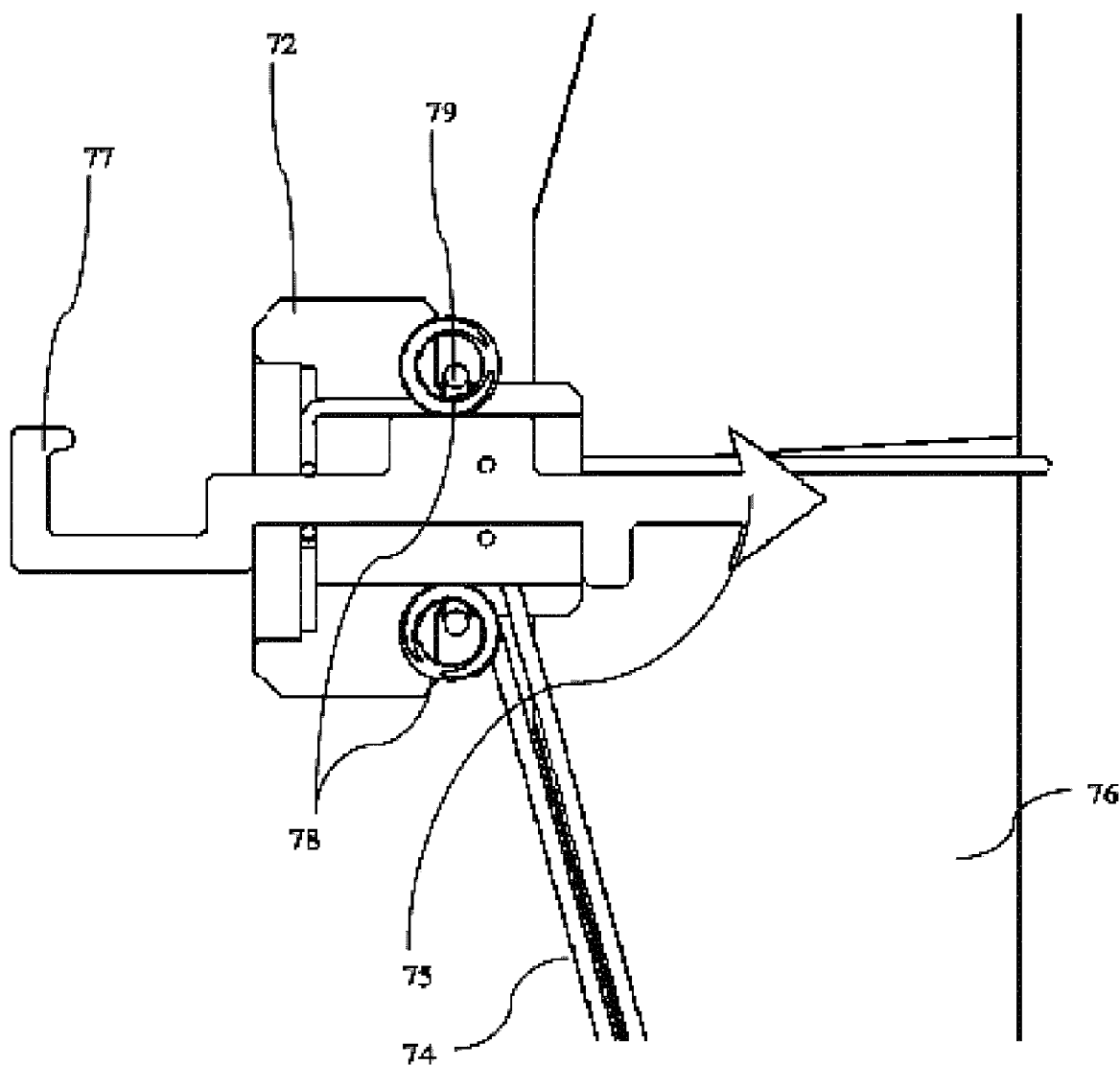
FIG. 9 is an enlarged sectional view of FIG. 8, focused on the mechanism.

Reference is now made to FIGS. 7-9 which schematic display another anchoring cleaning device. Anchorable cleaning device 70 comprises a tubular member 72. Four torsion springs 78 are fixed to the tubular member 72 by a ring 79. The wires of the torsion spring 78 extend to form four arms 74 which hold in place a piece of cleansing material 76 which is attached by means of a biocompatible adhesive. The torsion springs 78 allow the deployments and un-deployment of the device, such that when undeployed, the arms 74 can be reversibly folded towards each other, thus folding the cleansing material 76, so that the whole device can enter the sleeve (166) of an introducer device 160. Within the tubular member 72 resides an arrow shaped tack 75 with a hook at its proximal end 77 for engaging introducer device 160. The device 70 can be anchored to the undersurface of the cavity wall by piercing it with the arrow shaped tack 75.

Figure 10:
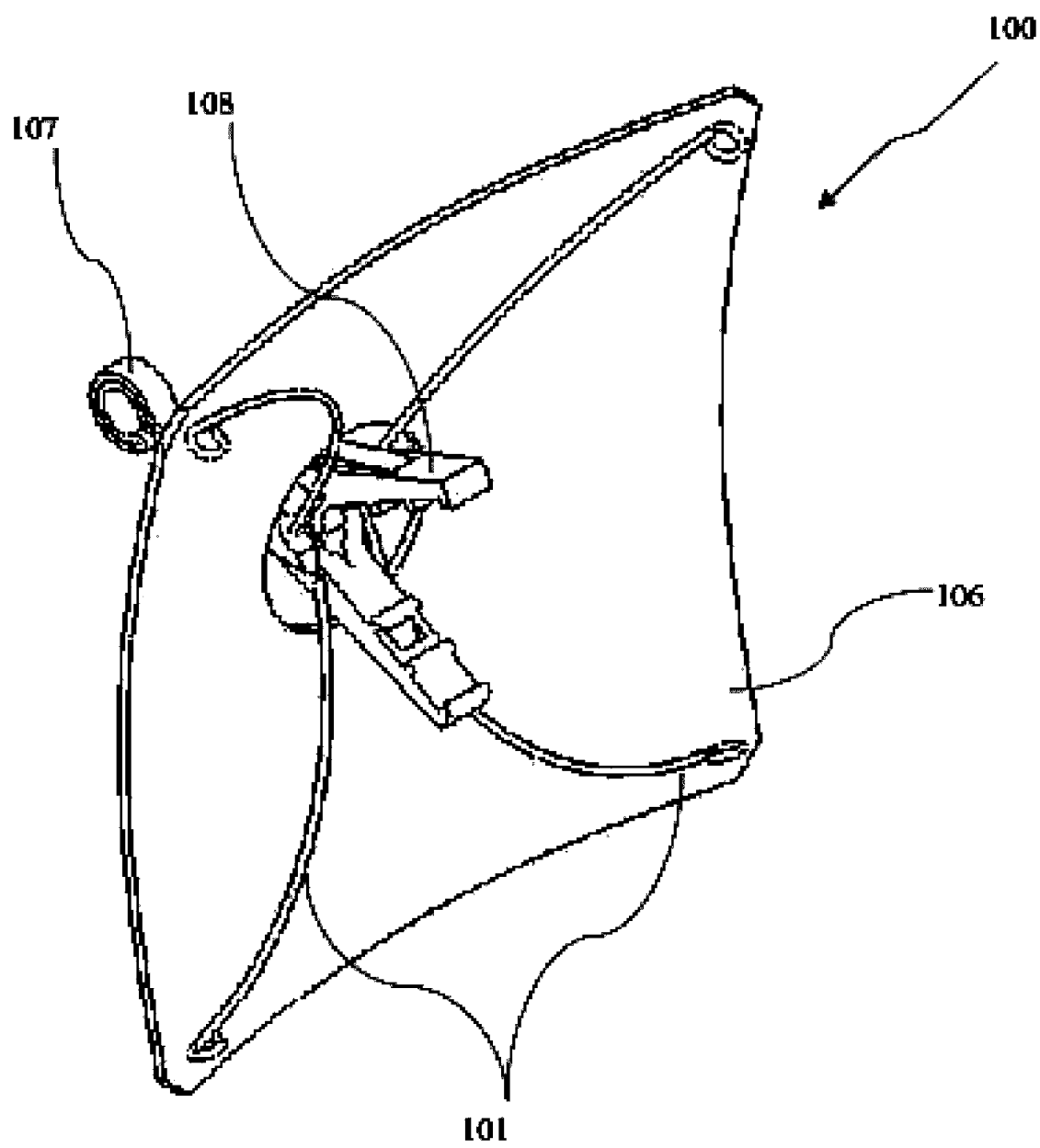
FIG. 10 is a perspective schematic view of an anchorable cleaning device, according to yet another embodiment of the present invention, in its open configuration.
Figure 11:
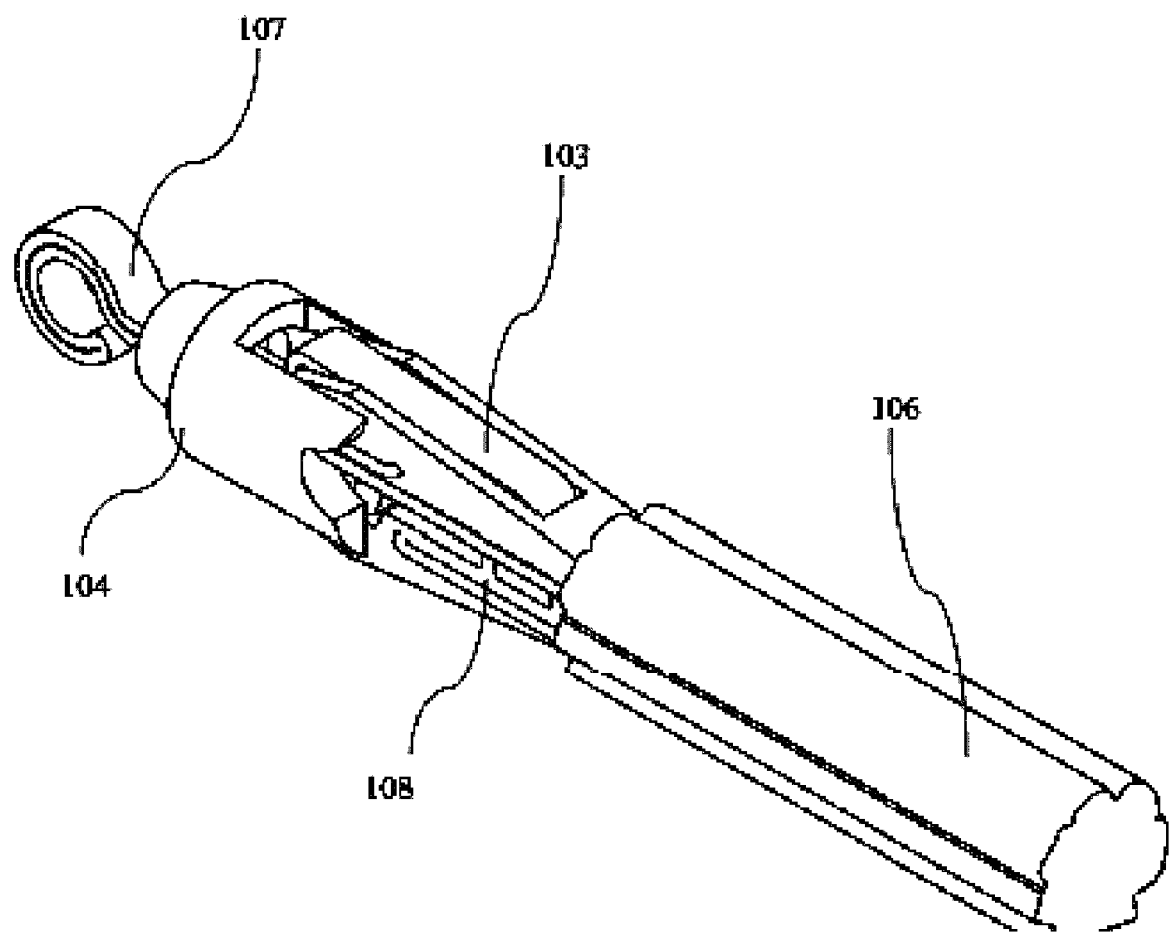
FIG. 11 is a side view of the same.
Figure 12:
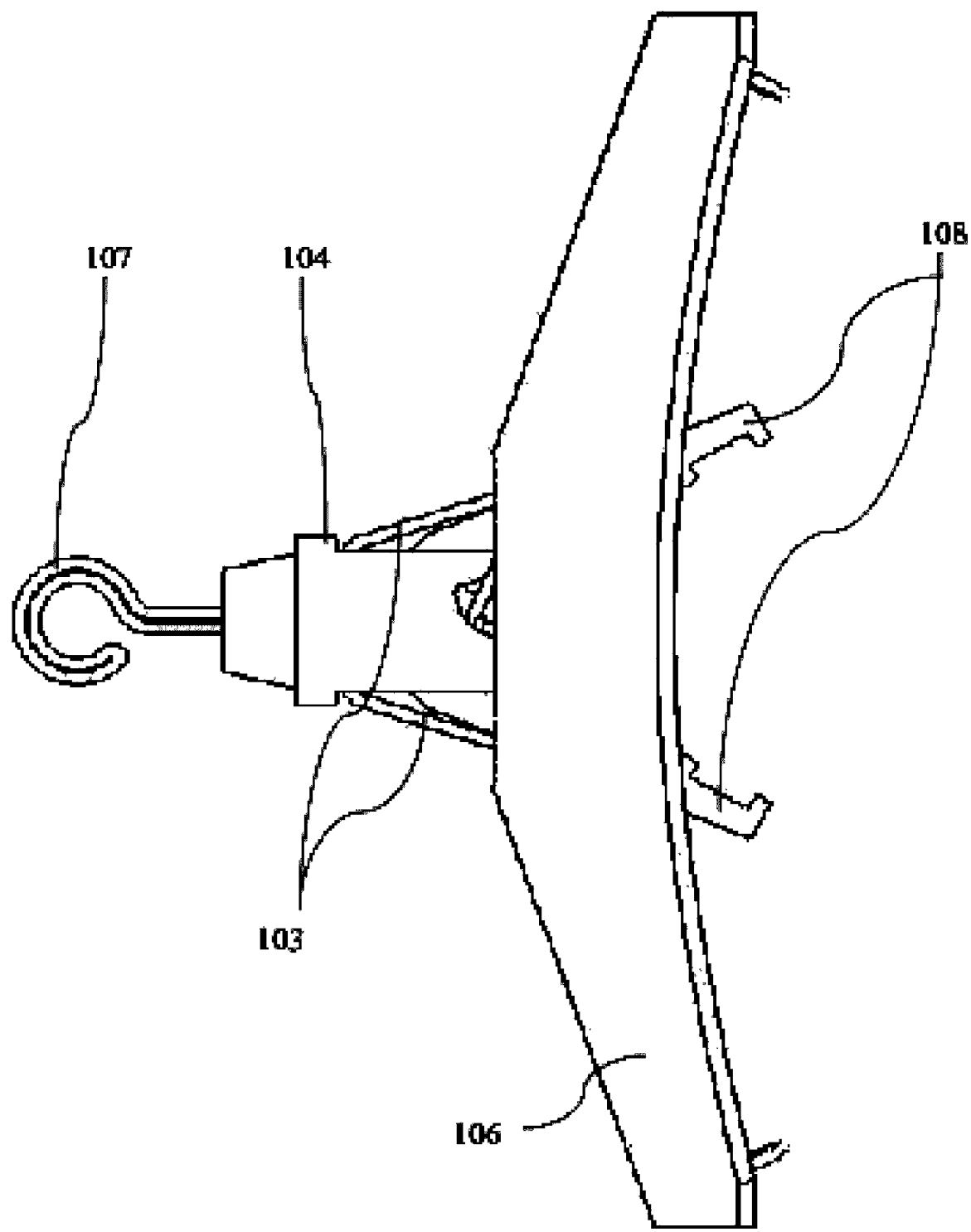
FIG. 12 is a perspective view of the same in its closed configuration.

Reference is now made to FIGS. 10-12 which schematic display another anchoring cleaning device. Anchorable cleaning device 100 comprises a tubular member 104. A cleaning means 106 is extended and supported by wires 101 which attach to the body, so that the wires can be reversibly folded towards each other 106 so that the whole device can enter the sleeve (166) of an introducer device 160. Two jaws 108 extend from the body to enable anchoring of the device by grasping the tissue at the desired location. A hook 107 at the proximal enables engaging an introducer device 160 so that by applying a pulling force on the hook the jaws are actuated and open about a central axis. The jaws tend to be in a closed state due to the elastic force applied by the leaf-spring 103 attached to each jaw.

Figure 13:
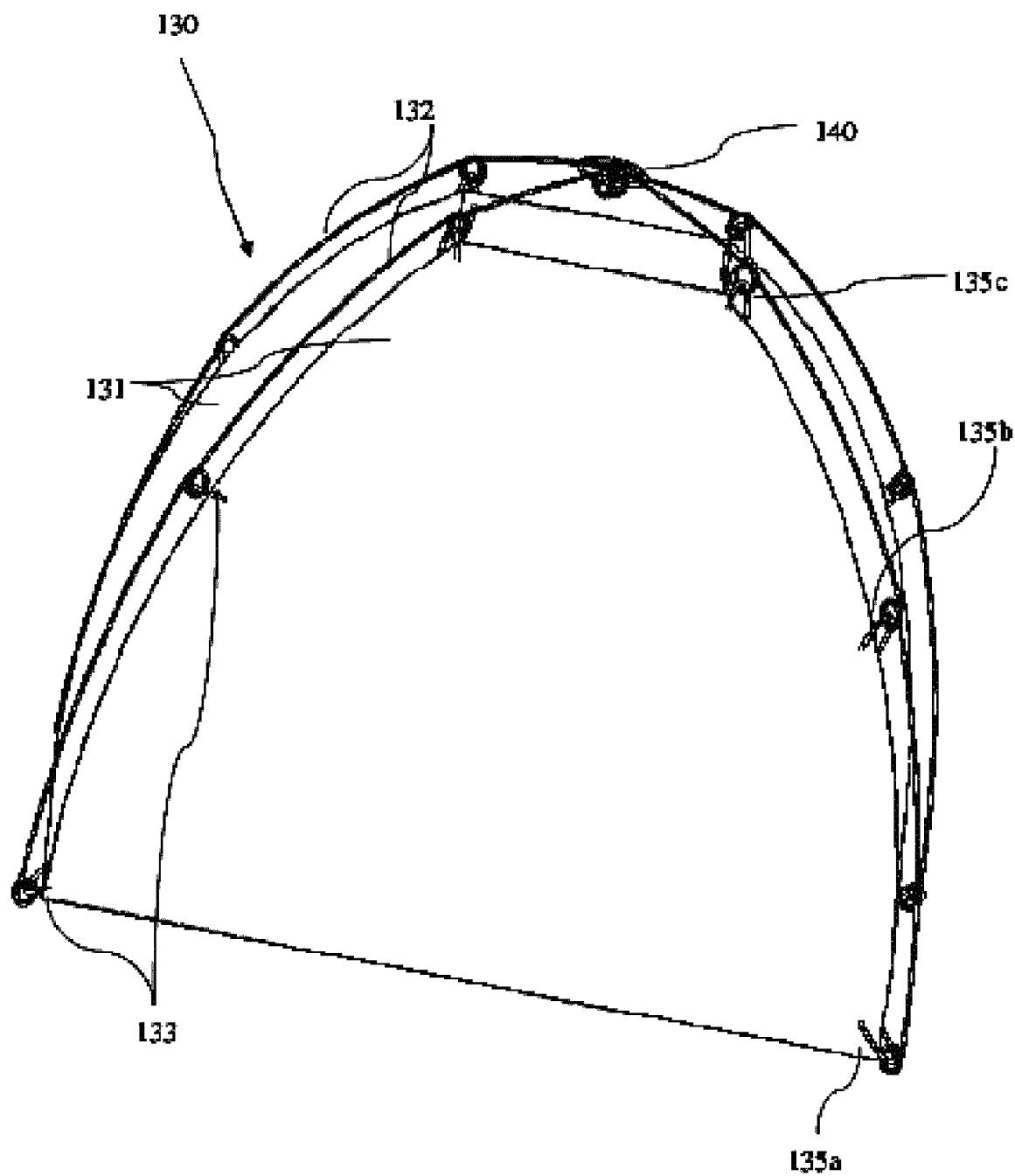
FIG. 13 is a perspective schematic view of a dome-tent shaped device with cleaning material on its sides in its deployed configuration, according to one embodiment of the present invention.
Figure 14:
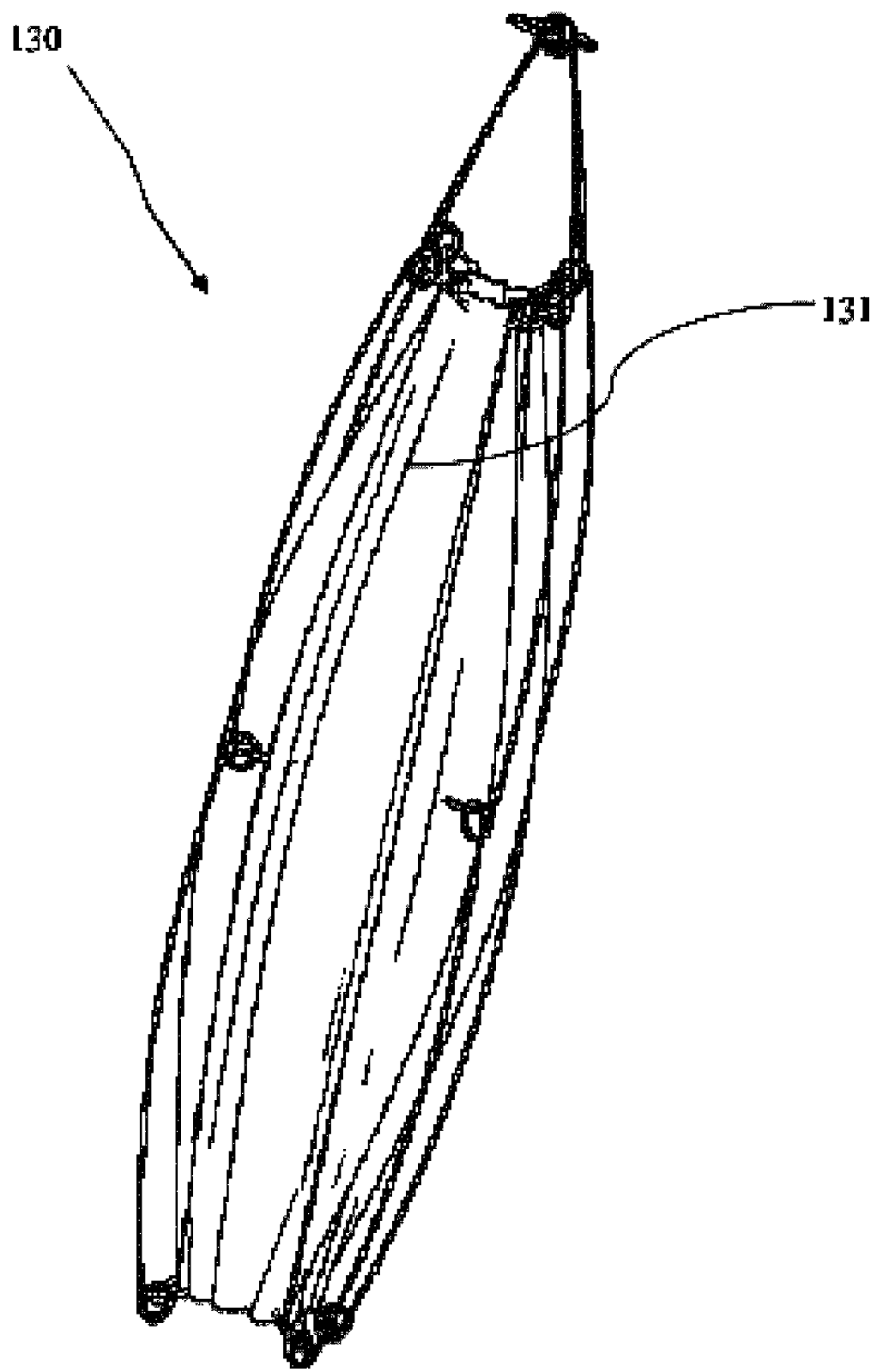
FIG. 14 is a perspective schematic view of the dome-tent shaped device in its undeployed configuration.
Figure 15:
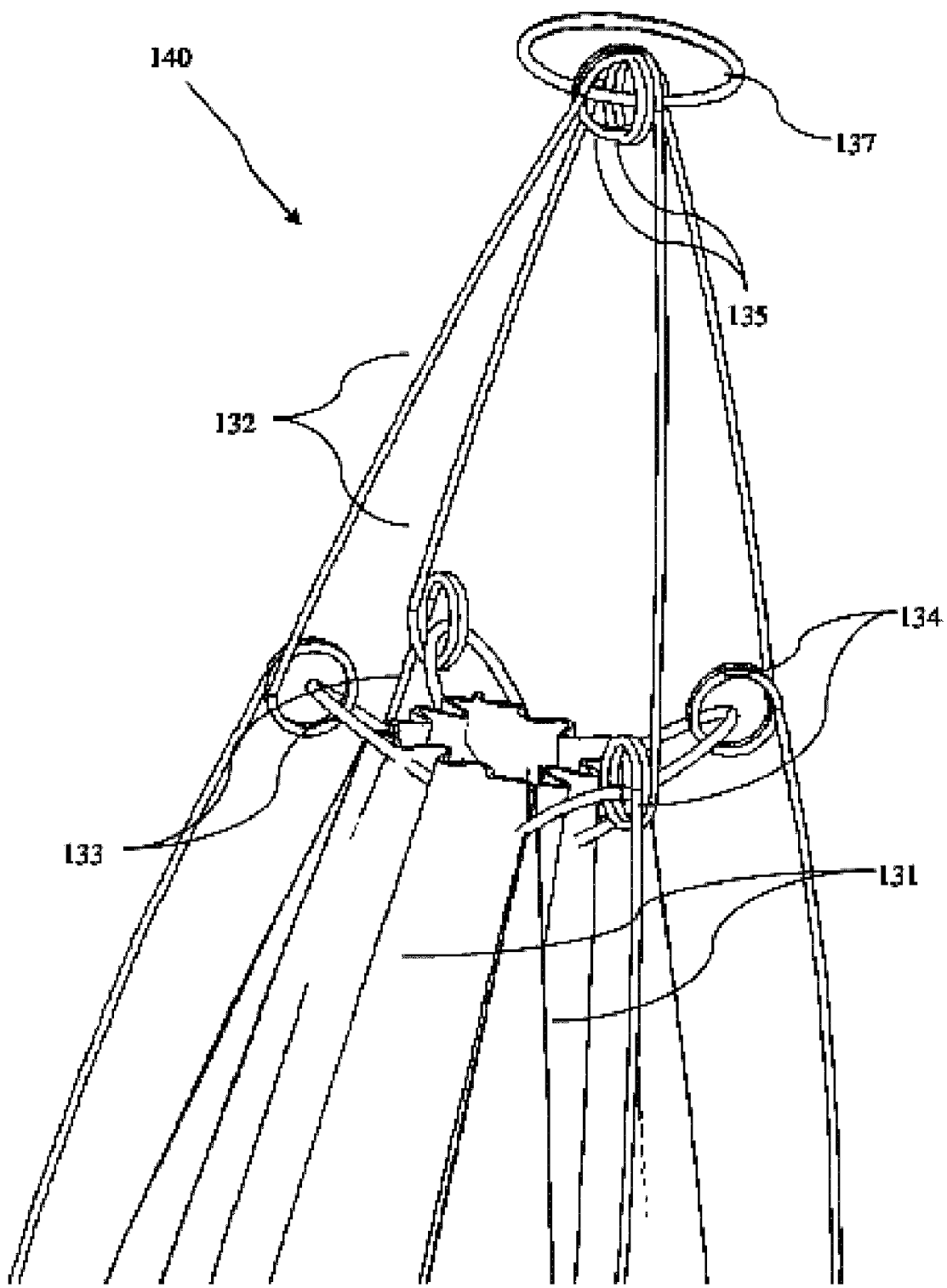
FIG. 15 is an enlarged view of FIG. 14, focused on the proximal end of the undeployed dome-shaped device.

Reference is now made to FIGS. 13-15 which schematically display a dome-tent shaped laparoscope cleaning device 130. The sides 131 and bottom of the device are made of a cleansing material (i.e. cloth). The sides 131 of the device are stretched out by two wire arcs 132. The arcs are attached to the sides by means of loops of thread 133 sewn through the sides and passing through torsion springs 134 at three points along each side: distal 135a, middle 135b and proximal 135c. The torsion springs provide an attachment point for the thread loops as well as elasticity for the wires. At the most proximal end 140 of the device a thread loop 137 joins the two proximal torsion springs 135 of the arcs 132. The loop can be engaged by a rigid metal hook inserted through a trocar (such as the "J" shaped hook commonly used for electrosurgery). Pushing the hook will eject the device 130 with its sides undeployed 131 deposited in the trocar into the abdominal cavity and it will deploy spontaneously. By means of the hook, the device can be moved within the abdominal cavity and repositioned during surgery. The device is removed from the patient's body through a trocar by pulling on the hook, as the device collapses and is again undeployed within the trocar tube.

Cleaning of the laparoscope for all above mentioned embodiments can be achieved by performing wiping motions of the laparoscope tip on the surface of the cleansing material as needed.

Figure 16:
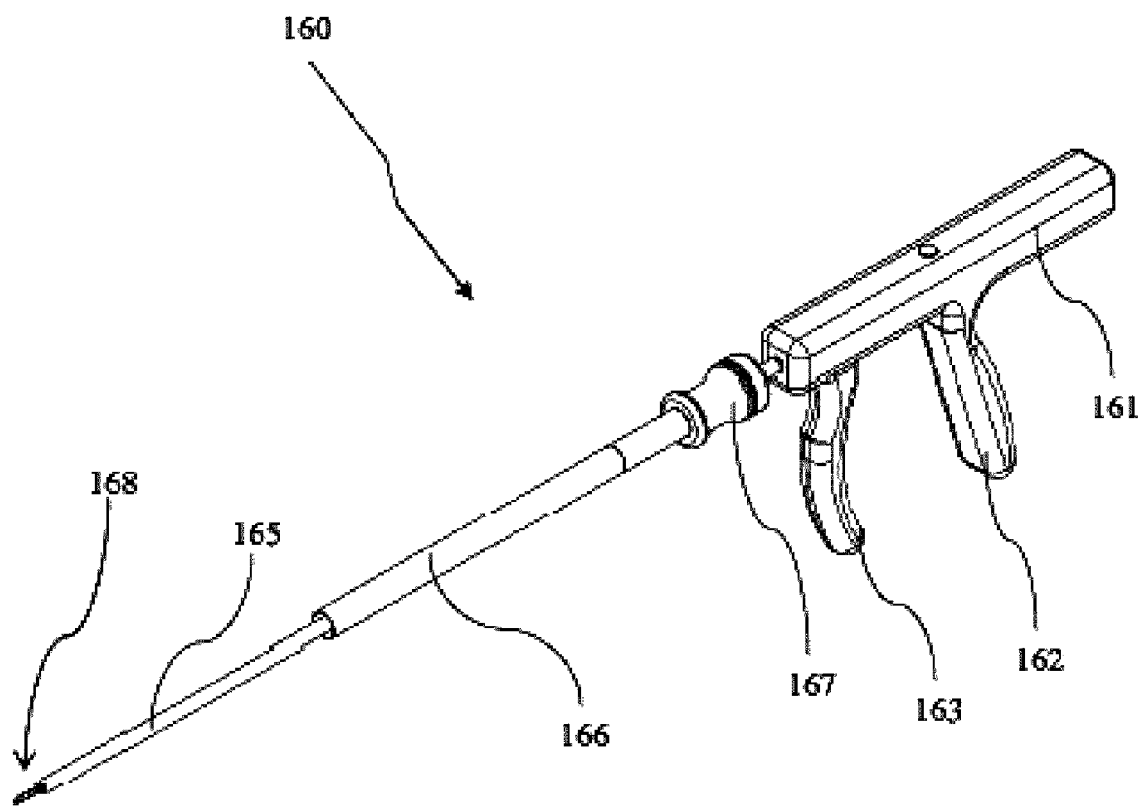
FIG. 16 is a perspective schematic view of the introducer for all aforementioned anchorable cleaning devices, according to one embodiment of the present invention.
Figure 17:
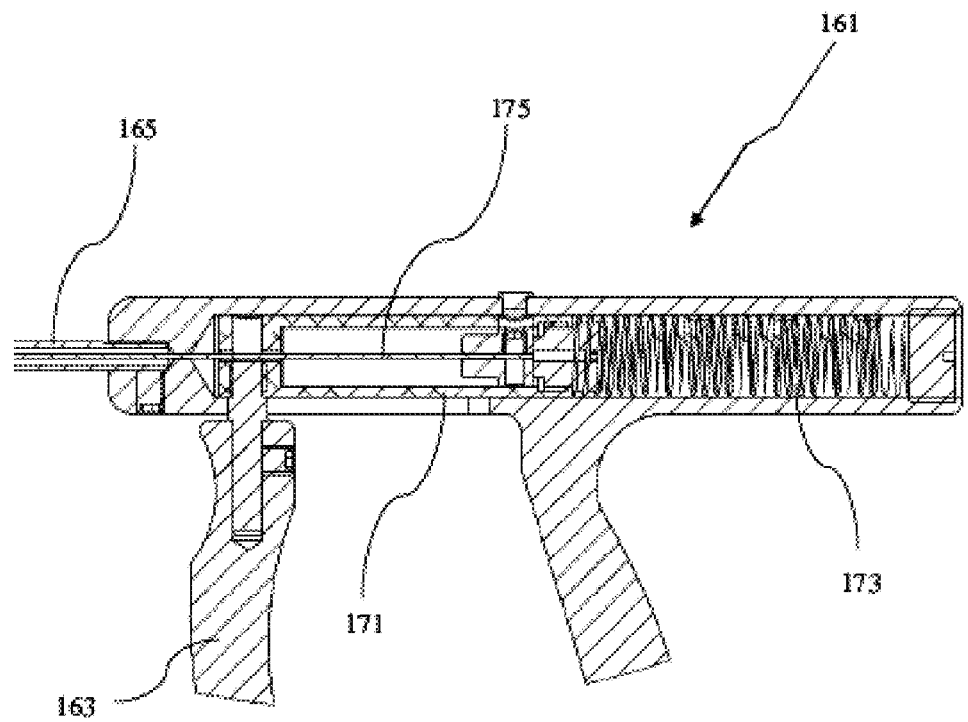
FIG. 17 is an enlarged cross sectional view, focused on the body of the introducer.
Figure 18:
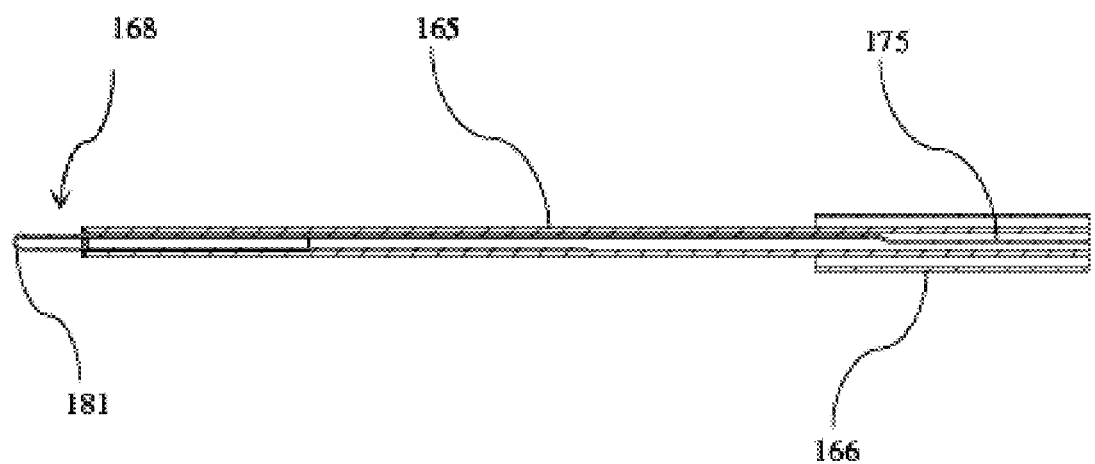
FIG. 18 is an enlarged cross sectional view, focused on the engaging end of the introducer.

Reference is now made to FIGS. 16-18 which schematically display the introducer 160 for all above mentioned anchorable camera cleaning devices. The introducer comprises a body 161 with a handle 162, a trigger 163, a tubular member 165 surrounded by a tubular sleeve 166 with a handle 162, and a distal engaging end 168. Within the body reside a piston 171, returning spring 173, and a wire 175 which runs along the axis of the introducer. The spring causes the piston 121 to stay at the distal end of the body when little or no force is applied at the trigger 163. When the trigger is pulled proximally, it pulls back the piston which in turn pulls back on the wire, and consequentially the spring contracts. From the distal end of the body 161 protrudes a tube 165 which is surrounded by a tubular sleeve 166. At its proximal end, the sleeve has a handle 162. The wire 175 exits the distal end of the tube while bent into a "U" shaped loop 181 for engaging the proximal end of the various embodiments of the anchorable cleaning device. Pulling the trigger 163 proximally consequentially retracts the wire loop at the distal end, thus actuating and enabling the manipulation of an anchorable cleaning device.

Figure 19:
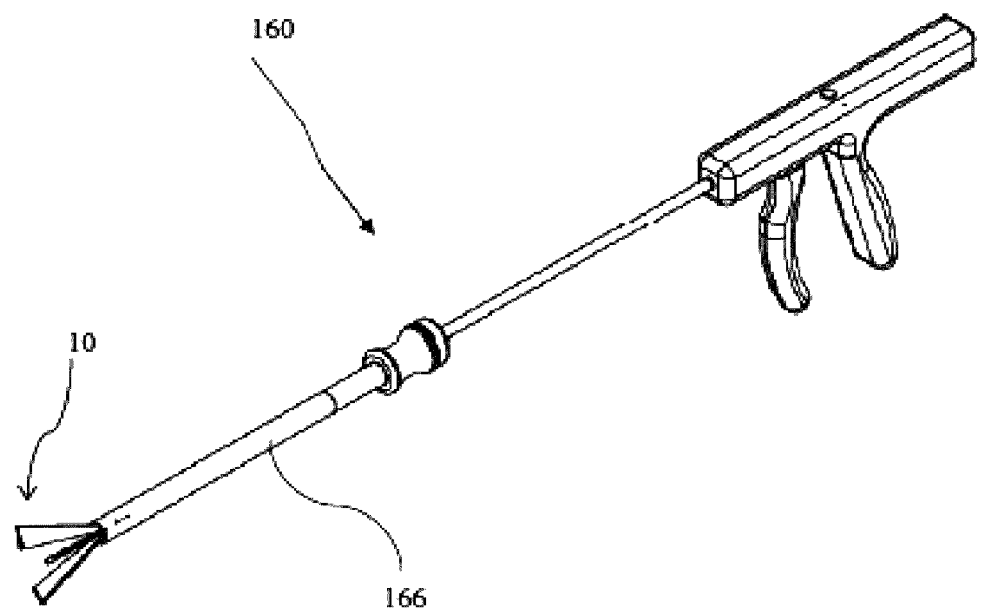
FIG. 19 is a perspective schematic view of an introducer engaging the anchorable cleaning device shown in FIG. 1, while it is in its closed configuration and partially within the sleeve of the introducer.
Figure 20:
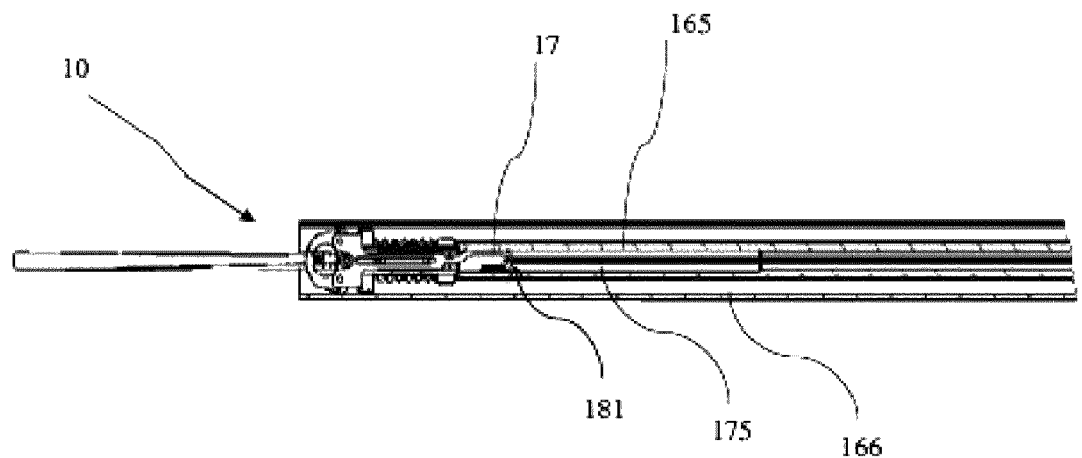
FIG. 20 is a top cross sectional view of the distal end of the introducer and engaged cleaning device.

Reference is now made to FIGS. 19-20 which schematically display the introducer 160 engaging with an anchorable cleaning device 10. The cleaning device is shown in a partially closed configuration, as it is inserted into the sleeve 166 of the introducer. In the cross sectional view of FIG. 20, it can be appreciated how the wire loop 181 engages the hook 17 of the cleansing device within the tube 165 of the introducer.

Figure 22:
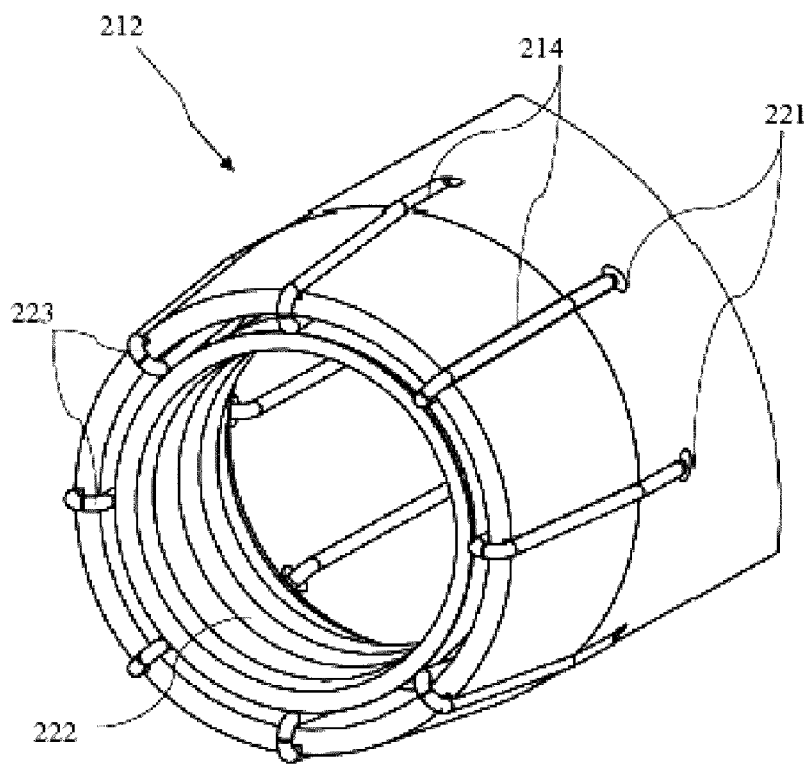
FIG. 22 is an enlarged view of FIG. 20 focused on the distal end of the trocar tube.
Figure 23:
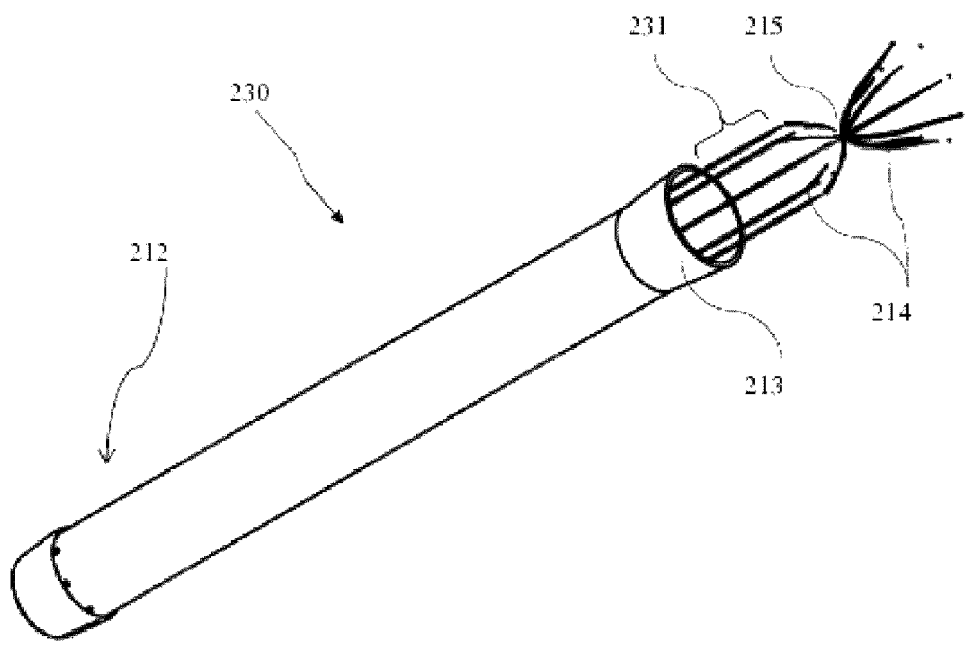
FIG. 23 is a perspective schematic view of the trocar tube with cleaning material at its distal end, in its deployed configuration.

Reference is now made to FIGS. 21-24 which schematically display an integrated trocar and a cleaning element. A trocar tube 210, through its proximal end 213 are inserted a plurality of threads 214 which are tied or joined at a central point 215. The threads run along the interior wall of the tube 210 exiting near the distal end 212 through holes 221. When undeployed, the threads continue along the outer wall of the tube 210 in grooves 225 and reenter into the tube at its distal tip 223. Inside the distal end 212 is a piece of cleansing element 222 (i.e. cloth) attached to the threads by means of biocompatible adhesive or sutures. The cleansing material is of a tubular form and while in its undeployed state it's adjacent to the inner wall of the distal end of the trocar tube (FIG. 22). When deployed, the threads are pushed distally to a certain length 231, this causes the distal part of the threads to recede and exit the interior of the distal end 212, thus exposing the cleansing element 222 and extending it along the outer wall of the distal end. Cleaning of the laparoscope can be achieved by wiping motions of the laparoscope tip on the surface of the cleansing material. The trocar tube 210 can be simultaneously used for other tools.

Figure 25:
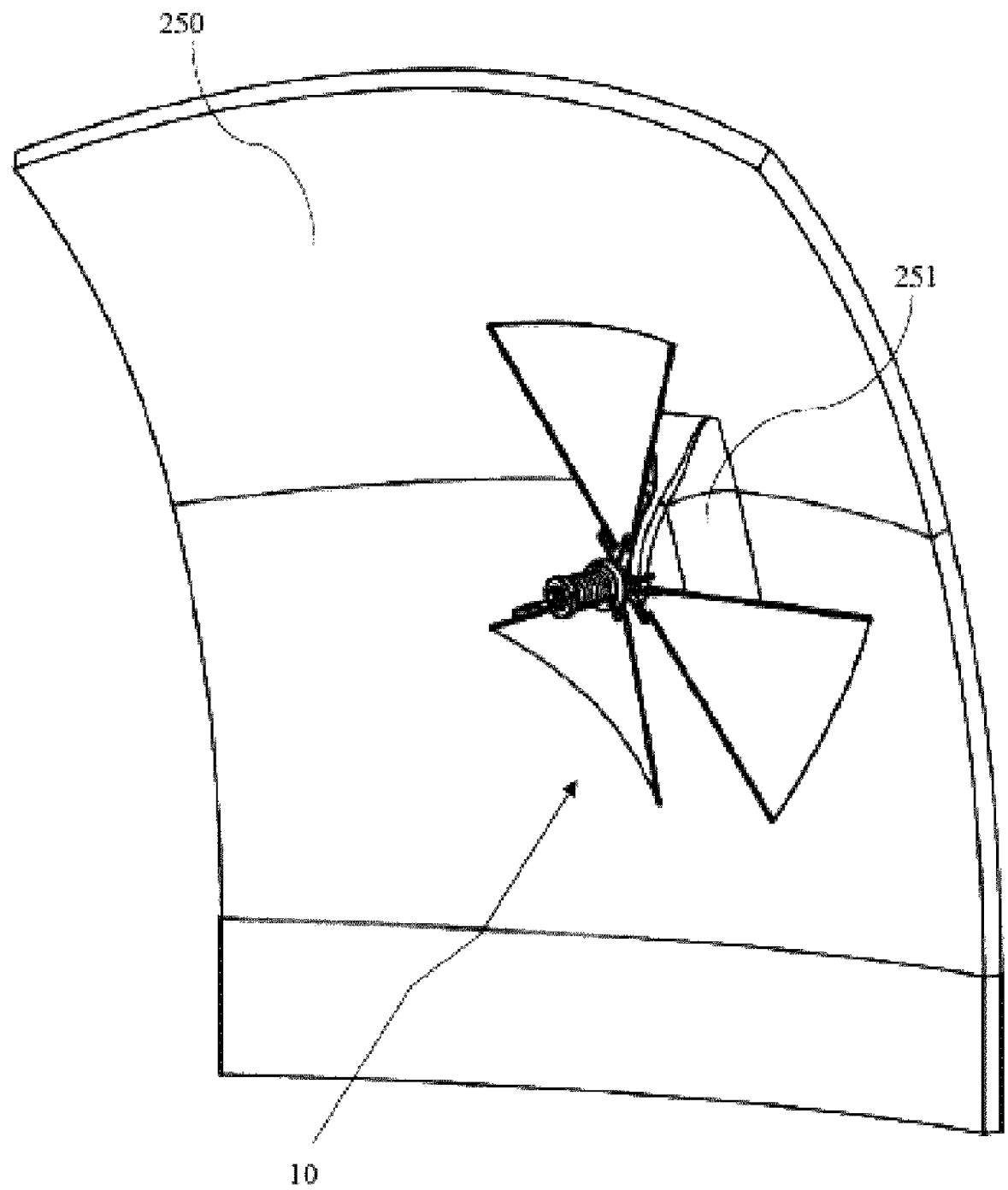
FIG. 25 is a perspective schematic view of an anchorable cleaning device attached to an internal cavity wall (i.e. peritoneum)
Figure 26:
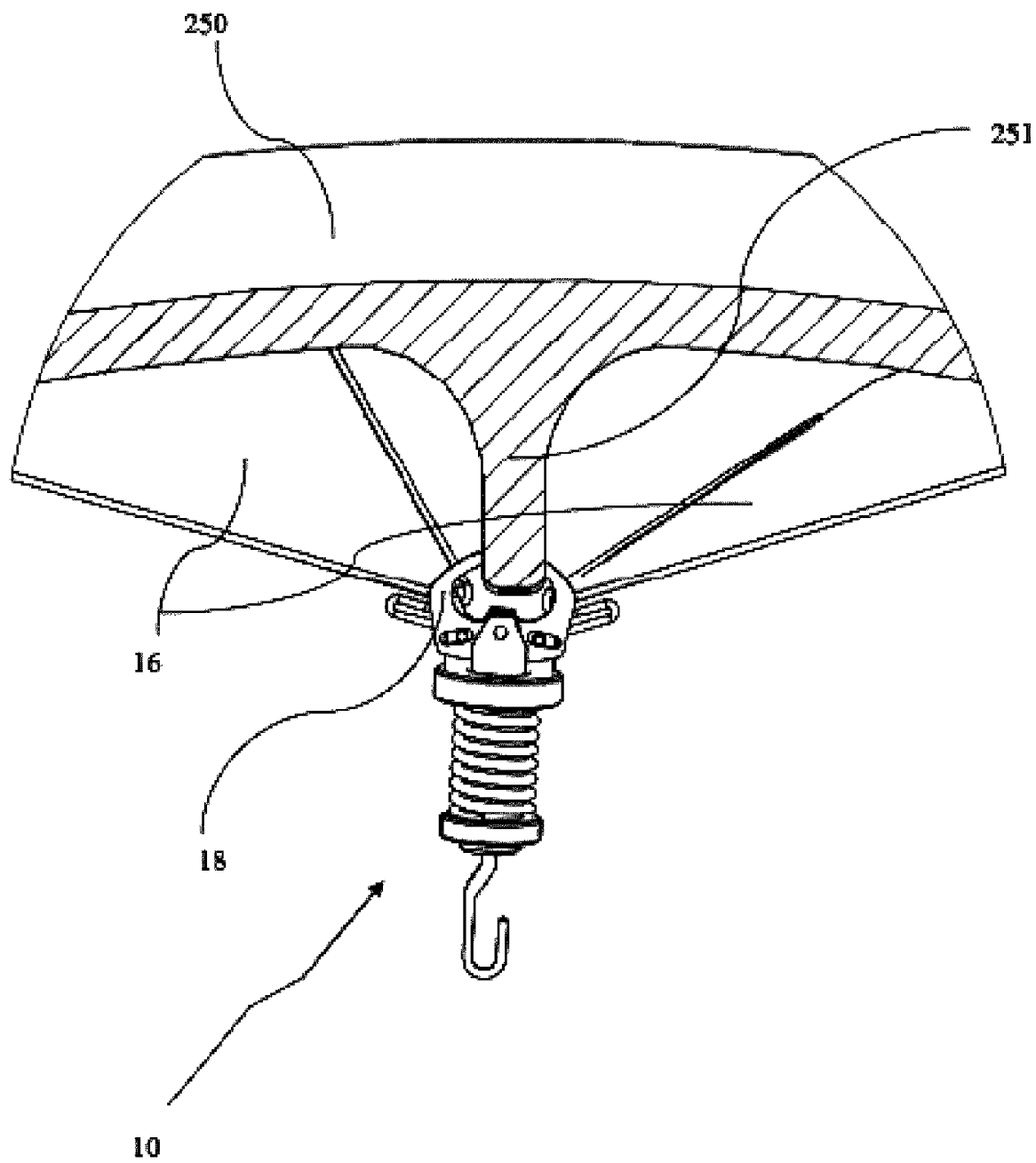
FIG. 26 is a top cross-sectional view of the cleansing device at its anchoring point.

Reference is now made to FIGS. 25 and 26 which schematically display an anchorable cleansing device 10 in its deployed configuration, such that it is attached and anchored to the wall 250 of a cavity within the body. The cleansing device is anchored by pinching a piece of tissue 251 by means of the jaws 18. The cleansing vanes 16 are spread out nearly parallel to the cavity wall.

Figure 27:
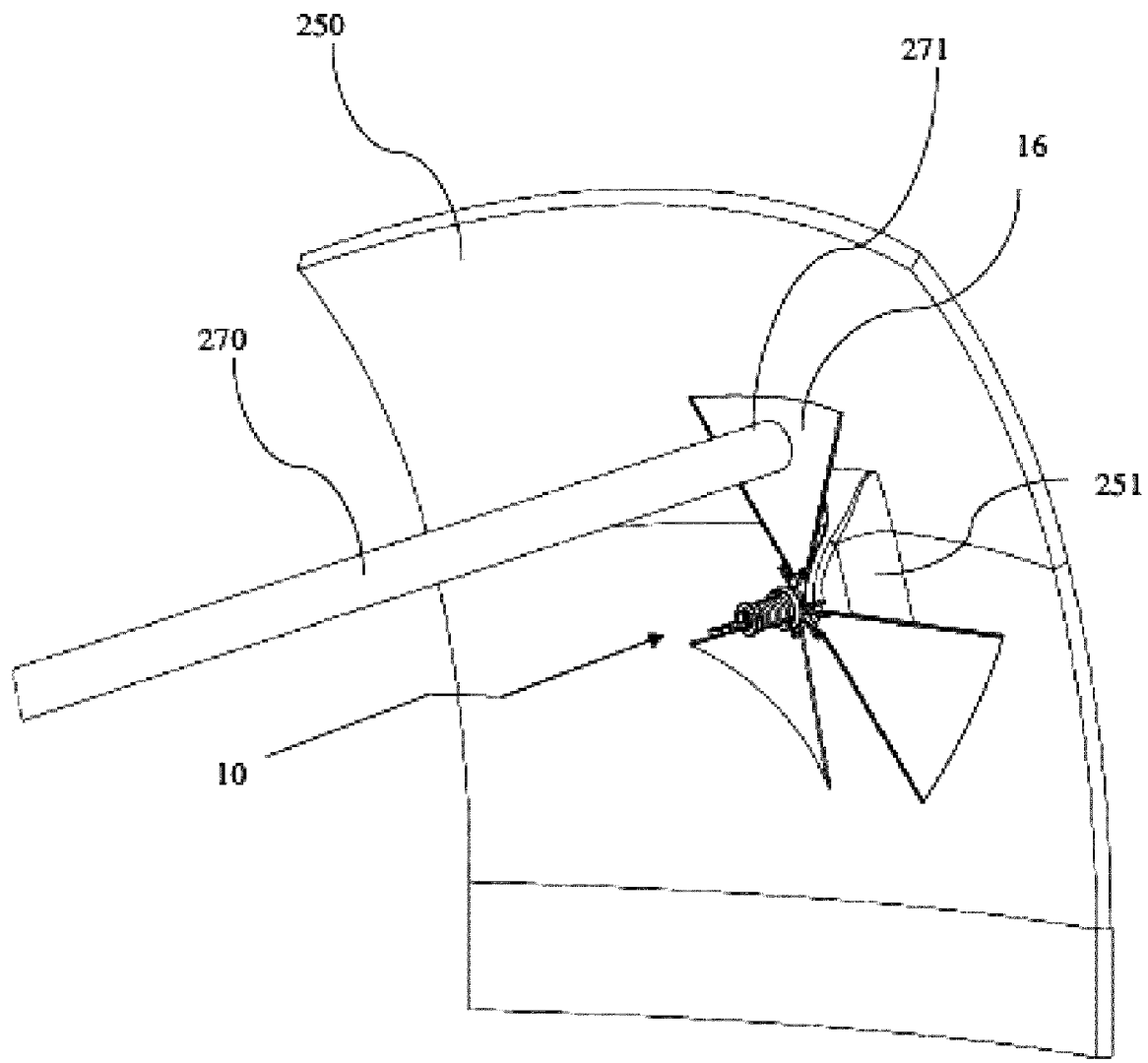
FIG. 27 is a perspective schematic view of the cleansing process of an endoscopic optical piece on an anchorable cleansing device attached to an internal cavity wall.

Reference is now made to FIG. 27 which schematically displays the cleansing process of a scope 270 on an anchorable cleansing device 10 anchored to the wall of an internal cavity 250. Cleansing is accomplished by rubbing the scope's optics located at its distal end 271 in a wiping movement on any of the cleansing vanes 16. This procedure can be repeated several times during surgery.

The present invention also provide a method for cleaning and/or improving and/or restoring visibility of surgical instruments, especially the scope lens and/or the tip of the scope and/or the cover of the scope and/or camera lens, useful for surgical procedures. At the first step the cleaning device according to any of the above is obtained. Next, the cleaning device is inserted through an incision into a body cavity and/or to an organ and/or to a hollow body organ and/or natural/artificial orifices and/or spaces and/or post operative spaces in its closed configuration via said introducer. At the next step, the introducer is disconnected from the cleaning device. At the final step, the surgical instrument scope lens and/or the tip of the scope and/or the cover of the scope and/or the camera lens is cleaned by wiping the surgical instrument over the cleaning device.

The invention claimed is:

1. A standalone cleaning device for cleaning at least a portion of a surgical instrument, within a body cavity during minimal invasive surgical procedure, said standalone cleaning device is characterized by a proximal end and a distal end; said distal end comprising:
   (a) at least one cleansing means; said at least one cleansing means is characterized by an un-deployed configuration in which said device is inserted into said body cavity; and, a deployed configuration in which said portion of said surgical instrument is cleaned; said cleansing means are adapted to be reversibly transformed from said deployed configuration to said un-deployed configuration and from said un-deployed configuration to said deployed configuration;
   (b) at least one anchoring means for at least partially reversibly anchoring said standalone cleaning device to an anchoring point; said anchoring point is located in an internal body cavity, such that creation of an opening at the location of said anchoring point for said cleaning is prevented;
   said proximal end comprising actuation means adapted to reversibly activate said anchoring means to provide said anchoring of said standalone cleaning device to said tissue within said body cavity;
   said cleaning of said surgical instrument is obtained by wiping motions of said portion of said surgical instrument over said cleansing means within said body cavity, such that the removal of said surgical instrument during said surgical procedure for cleaning necessity is avoided.

2. The standalone cleaning device according to claim 1, wherein said standalone cleaning device is shaped as a tent.

3. The standalone cleaning device according to claim 1, wherein said cleansing means automatically reconfigure from said un-deployed configuration to said deployed configuration upon introduction into said body cavity.

4. The standalone cleaning device according to claim 1, additionally comprising means adapted to manually and reversibly reconfigure said cleansing means from said deployed configuration to said un-deployed configuration and from said un-deployed configuration to said deployed configuration.

5. The standalone cleaning device according to claim 1, wherein said anchoring means are selected from a group comprising mechanical anchoring means, magnetic anchoring means, suction anchoring means, adhesive anchoring means, or any combination thereof.

6. The standalone cleaning device according to claim 1, wherein said actuation means is a hook or loop actuation means adapted to engage with an introducer (160).

7. The standalone cleaning device according to claim 1, wherein said proximal end and a distal end are coupled together by at least one shaft, said shaft adapted to reciprocally move along said main longitudinal axis of the same; said shaft is at least partially encapsulated by at least one sleeve-like enveloping compression spring;
   said anchoring means comprising at least one movable jaw, one end of said movable jaw pivotably connected to said shaft such that said movable jaw is characterized by at least one open configuration and at least one closed configuration; and can be reversibly transformed between said open configuration and said closed configuration by linear motion of said actuation means such that (i) said shaft is linearly moved; and, (ii) said compression spring is compressed or released such that said at least one movable jaw is reconfigured;

wherein, when said compression spring is released, it at least partially envelopes said movable jaw, thereby bringing it into said closed configuration, and further wherein when said movable jaw is in said closed configuration, said standalone cleaning device has an essentially cylindrical profile and will fit within a standard 5 mm diameter trocar.

8. The standalone cleaning device according to claim 7, wherein said standalone cleaning device has a normally closed configuration and must be actuated in order to move said compression spring toward said proximal end, thereby ceasing to envelope said movable jaw and transforming said movable jaw to said open configuration.

9. The standalone cleaning device according to claim 8, wherein linear movement of said compression spring results in radial movement of said movable jaw.

* * * * *